(12) United States Patent
Fujimoto et al.

(10) Patent No.: US 8,501,199 B2
(45) Date of Patent: Aug. 6, 2013

(54) SYNTHETIC BLOCKING REAGENTS

(75) Inventors: Naho Fujimoto, Hamburg (DE); Niels Röckendorf, Bargfeld-Stegen (DE); Steffen Bade, Klein Rönnau (DE); Katrin Ramaker, Norderstedt (DE); Andreas Frey, Gross Niendorf (DE)

(73) Assignee: Forschungszentrum Borstel, Borstel (DE)

( * ) Notice: Subject to any disclaimer, the term of this patent is extended or adjusted under 35 U.S.C. 154(b) by 269 days.

(21) Appl. No.: 12/797,998

(22) Filed: Jun. 10, 2010

(65) Prior Publication Data

US 2010/0317048 A1    Dec. 16, 2010

(30) Foreign Application Priority Data

Jun. 10, 2009  (EP) .................................. 09007701

(51) Int. Cl.
*A61K 45/00*    (2006.01)
*A61K 31/00*    (2006.01)

(52) U.S. Cl.
USPC ........ 424/278.1; 564/505; 530/421; 424/78.3

(58) Field of Classification Search
None
See application file for complete search history.

(56) References Cited

U.S. PATENT DOCUMENTS 5,643,575 A * 7/1997 Martinez et al. ............ 424/194.1
2007/0032405 A1 * 2/2007 DeFrees ............................. 514/8

FOREIGN PATENT DOCUMENTS

| EP | 04771169.2 | 7/2004 |
| EP | 09007701.7 | 6/2009 |
| GB | 19880028982 | 12/1988 |
| WO | PCT/US2003/000945 | 1/2003 |
| WO | PCT/EP2006/010488 | 10/2006 |
| WO | PCT/EP2007/059228 | 9/2007 |

OTHER PUBLICATIONS

Bade et al., "Intranasal immunization of Balb/c mice against prion protein attenuates orally acquired transmissible spongiform encephalopathy," *Vaccine* 2006, 24: 1242-1253.
Frey et al., "A statistically defined endpoint titer determination method for immunoassays," *Journal of Immunological Methods* 1998, 221: 35-41.
Harkins and Jordan, "A Method for the Determination of Surface and Interfacial Tension From the Maximum Pull on a Ring," *J. Am. Chem. Soc.* 1930, 52(5): 1751-1772.
Kilpatrick, "Factors Affecting Cardiolipin Antibody Assays: Modification with Polyethylene Glycol Compound," *British Journal of Haematology* 1998, 100: 52-57.
Studentsov et al., "Enhanced Enzyme-Linked Immunosorbent Assay for Detection of Antibodies to Virus-Like Particles of Human Papillomavirus," *Journal of Clinical Microbiology* 2002, 40(5): 1755-1760.
European Search Report and Opinion issued Nov. 19, 2009 for European Patent Application No. EP 09007701.7, filed Jun. 10, 2009. (Applicant—Forschungszentrum Borstel Leibniz-Zentrum für Medizin und Biowissenschaften // Inventor—Fujimoto Naho) (9 pages).
Communication from Examining Division issued Feb. 16, 2012 for European Patent Application No. EP 09007701.7, filed Jun. 10, 2009. (Applicant—Forschungszentrum Borstel Leibniz-Zentrum für Medizin und Biowissenschaften // Inventor—Fujimoto Naho) (1 page).
Reply to Communication from Examining Division issued Jun. 4, 2012 for European Patent Application No. EP 09007701.7, filed Jun. 10, 2009. (Applicant—Forschungszentrum Borstel Leibniz-Zentrum für Medizin and Biowissenschaften // Inventor—Fujimoto Naho) (30 pages).

\* cited by examiner

*Primary Examiner* — Shafiqul Haq
(74) *Attorney, Agent, or Firm* — Ballard Spahr LLP

(57) ABSTRACT

The present invention concerns novel synthetic blocking reagents for the reduction of non-specific bindings in solid phase assays that rely on biological and specific recognition, e.g., in enzyme-linked immunosorbent assays (ELISAs). The invention provides the use of compounds as blocking reagents as well as kits comprising these compounds. The compounds comprise one or more poly(ethylene glycol) moieties, one or more alkyl- or aminoalkyl groups and another unit bridging the aforementioned groups, wherein the compound comprises at least one amino group.

3 Claims, 5 Drawing Sheets

A.

B.

SYNTHETIC BLOCKING REAGENTS

This application claims priority to European Patent Application No. EP 09007701.7 which is incorporated herein by reference in its entirety.

BACKGROUND

Solid phase based biomedical assays, especially ELISAs (enzyme-linked immunosorbent assays) are used very commonly in the field of clinical diagnostics and biological research. They are widely used analysing methods due to the ease and rapidity of the assay procedures. There are diverse materials used as supporting solid phase, e.g., (microtiter-) plates or particles (beads) made of polymers like polystyrene, polypropylene and other substances. Well-established tests on the market range from serological diagnosis of severe diseases (e.g., HIV, Hepatitis, TSE, Malaria, Tuberculosis) to routine controls in clinical chemistry (e.g., cholesterol, insulin, drug/pregnancy tests).

Many reagents or sample components in biological assays tend to adhere to the solid phase or to already immobilised reagents on the surface in an unintended manner. As such binding does not represent a part of the very specific ligand/receptor (e.g., antigen-antibody) recognition process, it is generally referred to as non-specific binding (NSB). NSB events (NSBs), especially of detection antibodies, potentially lead to false-positive signals, as they may occur even if one component of the intended recognition setup is missing. Such false-positives are inherent to the system and appear as an even background signal or simply "noise". On the other hand, NSBs may disturb the recognition process between ligand and receptor (e.g., antigen and antibody). While false-positives lower the specificity of an assay, a disturbance of the intended detection reactions by NSBs may also lead to a reduction of the signal-to-noise ratio, thereby generating false-negatives which in turn reduce the sensitivity of an assay.

In total, NSBs are a huge problem, because in many cases they are a major factor for inferior signal-to-noise ratios (S/N) of solid phase bioassays. Although the sensitivity and the detection limit of an assay often can be improved by using higher amounts of reagents, this approach is not advantageous in general, as it is costly, and it often causes higher NSB rates as well, thereby limiting the advantage of a higher sensitivity by a lower specificity. Additionally, the amount of sample provided is limited in many situations. Here in particular the reduction of NSB is of utmost importance in order to improve an assay.

Many different possibilities for the reduction of NSB are known in the state of the art. They range from modifying antibodies, changing the incubation conditions such as pH value, (pre-)purification of sample material or enrichment of the analyte of interest to treating the sample with serum or heat. These methods are often tedious, very problem-specific and their success tends to vary with assay conditions and the reagents used, so that they need to be newly developed for each experiment and do not always exhibit the desired effect.

A very common procedure for the prevention of NSB is the saturation of the solid phase surface with a so-called blocking reagent. In general, solid phase surfaces used for bioanalytical assays are designed in such a way that adsorption of biological materials is very facile. In a first step of the assay, referred to as coating step, one assay component onto which further assay components shall bind in subsequent assay steps is adsorbed onto the surface of the solid phase. This coating component usually does not cover the entire surface of the solid phase. Consequently, an additional assay step, referred to as blocking step, is required, where remaining free space on the solid phase surface is covered by a so-called blocking reagent. If blocking is omitted all biological components present in the following incubation steps may become adsorbed on remaining free spots of the surface, thereby causing the main part of NSB.

By treating the solid phase with a blocking reagent after the coating step, the surface ought to be saturated and this way protected against adsorption of further material. The effectiveness of the blocking procedure may vary greatly and depends largely on the type of blocking reagent applied in the assay.

To date, many different blocking reagents are used and are commercially available. The most common ones include reagents from biological sources, such as animal sera, gelatine, skimmed milk, treated or non-treated proteins and protein fractions like bovine serum albumin (BSA), casein or casein hydrolysate, but also detergents and polymers like Tween20 or Poly(vinylpyrrolidone) (PVP) (Studentsov et al. (2002). Enhanced Enzyme-Linked Immunosorbent Assay for Detection of Antibodies to Virus-Like Particles of Human Papillomavirus. J. Clin. Microbiol. 40:1755-1760).

Blocking reagents provide a sufficient solution for many NSB problems, but the reagents available to date have drawbacks. Firstly, most blocking reagents are derived from biological sources and, thus, are not only heterogeneous, lot-to-lot variable and decomposable, but may also be subject to import and export restrictions due to potential biohazards of certain materials of biological origin. They also tend to cross-react and may even inhibit important recognition processes like streptavidin-biotin binding. Problems with cross-reactivity have led to the development of reagents like fish sera, which show less cross-reactivity with mammalian reagents. Some blocking reagents derived from biological material, e.g., skimmed milk, are known to possess very good NSB reducing abilities, but they may also decrease the specificity of the assay by covering or replacing the coating material.

Synthetic blocking reagents, e.g., Tween20, do not share these disadvantages of proteinaceous materials, but they are not sufficient in reducing NSB and could therefore not establish a solid market share.

In conclusion, blocking reagents are normally obligatory in a solid phase based immunoassay, but it is not easy to determine which reagent is the most appropriate one. Many experimental assays are still not used in routine applications, because the available blocking reagents are not effective enough and the sensitivity of detection is insufficient.

Sufficing specificity is equally difficult to attain. Often high specificity is only achieved by cutting back on sensitivity and/or by accepting some of the above mentioned drawbacks (e.g., lot-to-lot variability) of blocking reagents from biological sources).

SUMMARY OF THE INVENTION

The present invention concerns novel synthetic blocking reagents for the reduction of non-specific binding in solid phase assays that rely on biological and specific recognition.

The invention provides the use of compounds as blocking reagents as well as kits comprising these compounds. The compounds comprise one or more poly(ethylene glycol) moieties, one or more alkyl- or aminoalkyl groups and another unit bridging the aforementioned groups and wherein the compound comprises at least one amino group. The compounds are also referred to as novel blocking reagents in the context of the invention.

BRIEF DESCRIPTION OF THE DRAWINGS

FIG. 3A shows the state of the art blocking reagents. FIG. 3B shows novel blocking reagents according to the invention.

FIG. 4A shows the blocking effect of different blocking solutions on PVDF membranes. FIG. 4B shows the blocking effect of different blocking solutions on nitrocellulose membranes.

DETAILED DESCRIPTION

Figure 1:
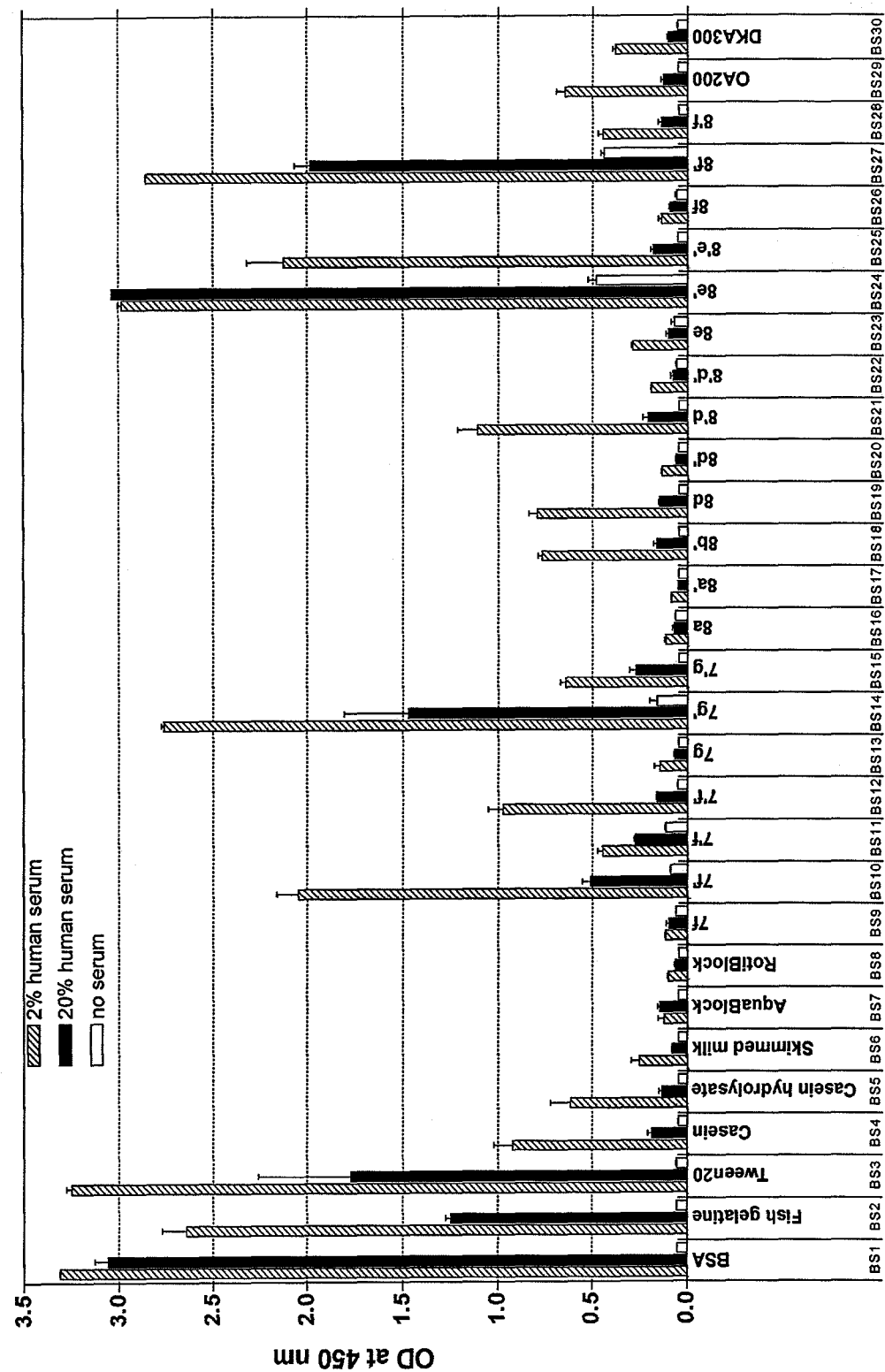
FIG. 1 shows results of a Specificity ELISA. Optical density generated by non-specifically bound immunoglobulin is given for 20% (v/v) and 2% (v/v) human serum in a specificity ELISA. Bars indicate mean+/−standard error (N=2 for BS9-28, and N=4 for BS1-8 and BS29-30).

Novel blocking reagents according to the invention outperform commonly used blocking reagents, especially in reducing non-specific binding without disturbing the desired specific recognition processes. They are also superior to reagents of biological origin, which are nowadays favoured, because, unlike these, the novel synthetic reagents show neither cross-reactivity nor lot-to-lot differences in the applications tested herein. The synthetic reagents according to the present invention are furthermore more stable at room temperature than most commonly used proteinaceous blocking reagents, in pure form as well as dissolved, are suitable for prolonged storage and are not subject to any import/export restrictions as they do not pose the risk of any biohazard whatsoever (e.g., reagents of bovine origin due to the issue of transmissible spongiform encephalopathies (TSE)).

In light of the state of the art, the problem solved by the inventors was the provision of synthetic novel blocking reagents that are superior to state of the art reagents. The reagents according to the invention do not exhibit the disadvantages of blocking reagents derived from biological materials, and they are able to efficiently reduce NSB while preserving the intended specific ligand-receptor (e.g., antigen-antibody) recognition. Thus, the novel blocking reagents increase sensitivity and specificity, thereby leading to an overall better signal-to-noise ratio (S/N) and lower detection limits.

The invention provides the use of a compound as a novel blocking reagent in a test system for the qualitative and/or quantitative determination of an analyte wherein the test system is based on specific binding between the analyte and a ligand thereof, wherein the analyte and/or the ligand is bound to a solid support either directly or mediated by covalent and/or adsorptive and/or non-covalent binding(s) to another molecule, wherein the compound is a compound of Formula I:

R$^1$-PEG-Bridge-Alkyl-R$^2$ wherein R$^1$ is a residue selected from the group consisting of —H, —CH$_3$, —CH$_2$CH$_3$, —CH$_2$CH$_2$CH$_3$ and —CH(CH$_3$)$_2$.

Bridge is a non-cyclical group comprising an amino group N$^1$ and/or an amide and/or an —O— ether, and R$^2$ is a residue selected from the group consisting of —H and an amino group N$^2$, which preferably is —NH$_2$, wherein the compound comprises at least one amino group, so that, if Bridge comprises no amino group N$^1$, R$^2$ is the amino group N$^2$;

or a salt of a compound of Formula I.

In a preferred embodiment of the invention, Bridge is a group comprising an amino group N$^1$. In this case, it is preferred that R$^2$ is —H. In another embodiment of the invention, Bridge is a group comprising an amide and/or an —O— ether, and R$^2$ is an amino group N$^2$, preferably —NH$_2$. The amino group N$^2$ may also be a mono-, di- or trisubstituted secondary, tertiary or quaternary amino or ammmonium group, where the substituent(s) may be identical or non-identical and selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)(CH$_2$CH$_3$) or —C(CH$_3$)$_3$. Bridge may be a linear or branched moiety.

Bridge may be selected from the group consisting of —NH—, —N(PEG-R$^3$)—, —N(Alkyl-R$^4$)—, —NHCH$_2$CH(Alkyl-R$^4$)—, NHCH$_2$CH[CH$_2$NH(PEG-R$^3$)]—, —NHCH$_2$C[CH$_2$NH(PEG-R$^3$)](Alkyl-R$^4$)—, —O—, —OCH$_2$CH(Alkyl-R$^4$)—, —OCH$_2$CH[CH$_2$O(PEG-R$^3$)]—, and —OCH$_2$C[CH$_2$O(PEG-R$^3$)](Alkyl-R$^4$)—, wherein R$^3$ is a residue selected from the group consisting of —H, —CH$_3$, —CH$_2$CH$_3$, —CH$_2$CH$_2$CH$_3$ and —CH(CH$_3$)$_2$, and R$^4$ is a residue selected from the group consisting of —H, —NH$_2$, and a mono-, di- or trisubstituted secondary, tertiary or quaternary amino or ammmonium group, where the substituent(s) may be identical or non-identical and selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)(CH$_2$CH$_3$) or —C(CH$_3$)$_3$, wherein preferably R$^3$ is the same as R$^1$. Preferably, R$^4$ is the same as R$^2$.

For example, Bridge can be selected from the group consisting of:

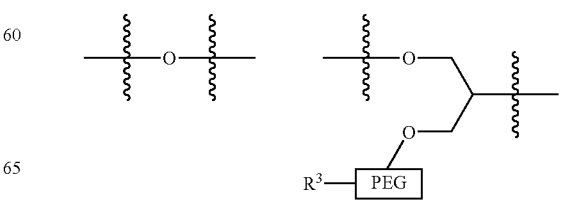

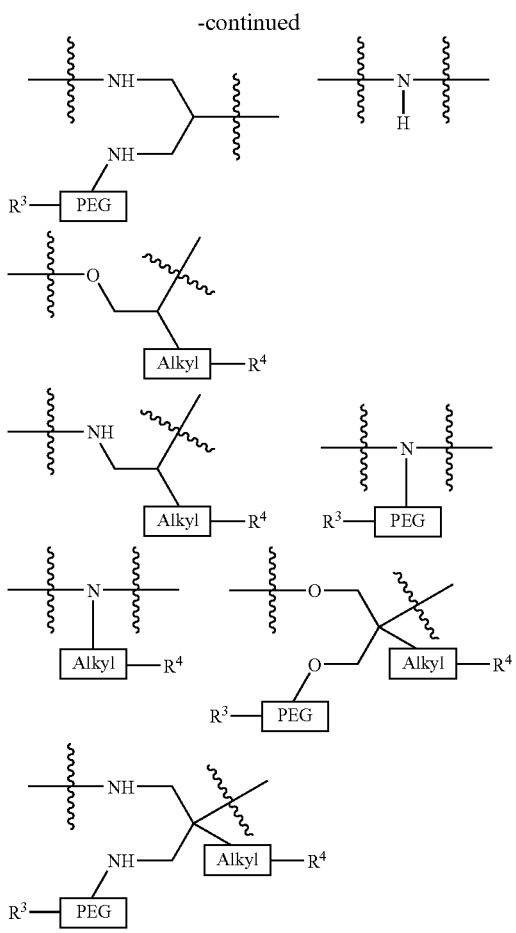

In these formulae, wavy lines indicate linkage to the other residues of the compound of the invention. On bonds open to the left hand side, the Bridge is linked to a PEG residue, and on bonds open on the right hand side, the Bridge is linked to an Alkyl residue.

Preferably, the only functional groups comprised in the Bridge are one or more (in particular, two) amine or —O— ether moieties. If more than one amine is present, the amines may be either a primary amine, a secondary amine, a substituted tertiary amine, or a substituted quaternary amine. The compound preferably does not comprise cyclic groups, esters or other, non-mentioned functional groups.

At the end of the Bridge and/or in the Bridge, one, or, if applicable, more (e.g., two) Alkyl group(s) and/or one or, if applicable, more (e.g., two) PEG group(s) are linked to the amine or —O— ether either directly or by a linear or branched alkyl-containing unit with 1, 2, 3 or 4 covalent bonds.

PEG stands for poly(ethylene glycol). It is a linear or branched poly(ethylene glycol) unit, preferably, a linear poly (ethylene glycol), i.e., it comprises oxyethylene units —(OCH$_2$CH$_2$)$_n$—, wherein PEG is linked to Bridge in the direction so that the structure is —(OCH$_2$CH$_2$)$_n$-Bridge, with n being a variable integer indicating the number of the average quantity of repeats of the polymer. Poly(propylene glycol) (PPG) units can be used instead of poly(ethylene glycol) units.

PEG may be a mono- or polydisperse polymer. In this context, polydisperse materials are defined to possess a molecular mass distribution, while monodisperse materials show a single molecular mass. Polydisperse polymers are common due to the technical manufacturing process of polymerisation.

PEG preferably has an average molecular weight of at least 300 Da, in particular, 300-3,500 Da, preferably, 400-2,500 Da. For example, PEG groups may have an average molecular weight of about 400-600 Da, 600-1,200 Da, 800-1,400 Da, 1,000-1,600 Da or 1,500-2,500 Da. Preferably, if a compound comprises more than one (e.g., 2) PEG groups, they both are similar or identical in average size, i.e., they were synthesised under the same reaction conditions.

$R^1$ and $R^3$ preferably are —H, especially if the compound is industrially produced. $R^1$ may also be —CH$_3$.

Alkyl may be a linear or branched, saturated or unsaturated, mono- or polydisperse alkylene moiety, preferably having an average alkyl chain length of at least 10 carbon atoms, in particular, of 10-26 carbon atoms, preferably of 12-20 carbon atoms. In this context, alkylene is a hydrocarbon group with two open chemical bonds available for linkage to other groups, such as an alkane-α-ω-diyl moiety. Preferably, Alkyl is a linear alkylene moiety —(CH$_2$)$_n$— with n being the average number of C-atoms. It is preferred that Alkyl is not substituted, except for the linkage to $R^2$ or $R^4$. It is preferred that Alkyl is saturated or comprises one —C=C— bond. Polydisperse alkylene units are common in materials of natural source, e.g., fatty acids.

In one embodiment, Alkyl is selected from —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, —(CH$_2$)$_{20}$—. Alkyl may also be an alkylene moiety derived from fats and fatty acids, e.g., from lard, butter, coconut oil, palm oil, soybean oil, olive oil, corn oil, sunflower oil, rapeseed oil, peanut oil, cottonseed oil. Alkyl can be derived from, e.g., myristoleic acid, palmitoleic acid, oleic acid, elaidic acid, linoleic acid, α-linoleic acid, arachidonic acid, eicosapentaenoic acid, erucic acid, docosahexaenoic acid or nervonic acid. Alkyl may also be a polydisperse linear alkylene group —(CH$_2$)$_n$— having an average alkyl chain length of 10-16 carbon atoms.

In the use of the invention, the compound may be selected from the group comprising

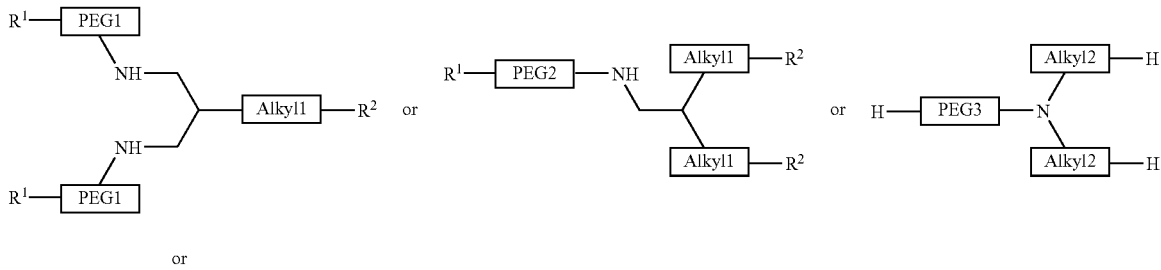

or

-continued

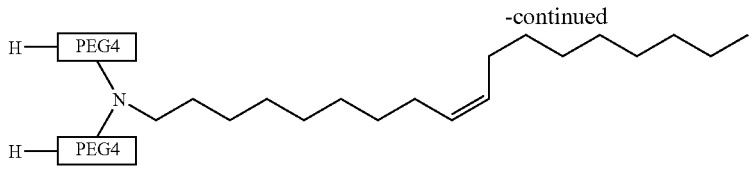

wherein R$^1$ is —CH$_3$,
R$^2$ is —H,
Alkyl 1 is a linear alkylene group selected from —(CH$_2$)$_{12}$— and —(CH$_2$)$_{20}$—,
Alkyl 2 is a linear polydisperse alkylene group —(CH$_2$)$_n$— with an average chain length of 10-16 carbon atoms,
PEG 1 is a linear poly(ethylene glycol) with an average molecular weight of 400-700 Da,
PEG 2 is a linear poly(ethylene glycol) with an average molecular weight of 400-700 Da or 1,500-2,500 Da,
PEG 3 is a linear poly(ethylene glycol) with an average molecular weight of 1,000-1,600 Da,
and PEG 4 is a linear poly(ethylene glycol) with an average molecular weight of 300-600 Da.

The compound may have a symmetrical structure, i.e., if two Alkyl-residues are present, they may have the same chain length if they are monodisperse and/or they may be similar or identical in size if they are polydisperse; the same applies if two PEG groups are present.

Throughout the invention, it is preferred that the critical micelle concentration (n/v) of the compound in D-PBS (Dulbecco's phosphate buffered saline, 1.47 mM KH$_2$PO$_4$, 8.10 mM Na$_2$HPO$_4$, 137 mM NaCl, 2.68 mM KCl, pH 7.4) is 0.02-1 mmol/L, preferably, 0.05-0.5 mmol/L and, more preferably, 0.08-0.27 mmol/L. These parameters were measured via tensiometry with the Du Noüy ring method (Harkins et al. (1930). A method for the determination of surface and interfacial tension from the maximum pull on a ring. J. Colloid Interface Sci. 52: 1751-1772).

The test system in which the compound is to be used as a novel blocking reagent is intended for the qualitative and/or quantitative determination of an analyte in a sample based on specific binding between the analyte and a ligand thereof, wherein the analyte and/or the ligand is bound to a solid support either directly or mediated by covalent and/or adsorptive and/or non-covalent binding(s) to another molecule. Such a test system may also be designated "assay" in the context of the invention. The sample can be of biological origin, e.g., it may be a sample analysed for medical/diagnostic reasons, e.g., blood, serum, sputum, liquor, urine, faeces, extracts or samples from the environment, or a dilution of the sample in water or a physiological buffer.

The test system may constitute any type of solid phase assay, particularly one in which capture molecules that are specific for an analyte are immobilized on a solid phase. Thereby an analyte can be selectively bound from fluid media and unbound components can be removed from the solid phase by washing. Subsequently, the analyte can be detected by using labelled probes. Preferably the test system may be selected from, but not restricted to, the group comprising enzyme-linked immunosorbent assay (ELISA), fluorescence-linked immunosorbent assay (FLISA), fluorescent enzyme-linked immunosorbent assay (FELISA), fluorescence immunoassay (FLIA), Enzyme-Linked Immunosorbent Spot assay (ELISPOT), enzyme immunoassays (EIA), radioimmunoassay (RIA), Western Blot, Southern Blot and Northern Blot. The ligand and/or the analyte may be cells of animal, plant or insect origin or an oligo- or polynucleotide, a nucleic acid, e.g., DNA, or, a small molecule, e.g., a steroid (e.g., glucocorticoids or cholesterol), a hormone (e.g., epinephrine, progesterone or leukotriene) or a hapten (e.g. 2,4-dichlorophenoxyacetic acid, biotin, dinitrophenol or digoxigenin), a lipid (e.g., a phospho- or glycolipid), an oligo- or polysaccharide (e.g., galactose or glycans such as glycogen or amylose), an oligo- or polypeptide (e.g., a defensin or a hormone such as insulin), a protein (e.g., a lectin or an antibody) or derivatives or combinations (e.g., conjugates or mixtures) of any of the aforementioned substances. Peptides or proteins may be glycosylated. Preferably, ligand and analyte are an antibody and an antigen/hapten, or a lectin and a carbohydrate-containing structure, or vice versa. Hence, the preferred specific binding is the interaction between an antibody and an antigen/hapten or between a lectin and a carbohydrate-containing structure, e.g., a glycoprotein, but the test may also be based on the specific binding between a receptor and a ligand thereof, either of which may serve as ligand or analyte in the test of the invention. Preferably, ligand and/or analyte are derived from biological material, including purified matter from natural biological sources or from material modified by genetic engineering. Synthesis of the ligand and/or the analyte is also possible, e.g., in the case of peptides, proteins or nucleic acids.

In the assay, either ligand or analyte is immobilised on a solid phase by one of the means described before. If a ligand is immobilised, the analyte can be selectively bound out of a sample containing the analyte and unbound components can be removed from the solid phase by washing. The analyte can be subsequently detected by using labelled probes. This set-up is referred to as a "capture assay". Similarly, if an analyte is immobilised on a solid phase, a labelled or non-labelled ligand can be selectively bound from a liquid medium. A non-labelled ligand may then be detected by using labelled detection reagents. In a competitive or inhibitory assay, a reference system of any of the aforementioned designs with known quantities of reagents is set up and determined first. The analyte-containing sample is added in one of the reagent steps in a way that analyte molecules may compete with or inhibit reagent(s) of the reference system, and the signal deviation compared to the reference system is determined.

The solid support and/or its surface may be made from a material selected from, without being restricted to, the group comprising polystyrene, polypropylene, PVDF (polyvinylidenedifluoride), nylon, nitrocellulose, ceramics, metals, semi-metals, such as silicon, and glass, such as borosilicate glass, lead silicate glass and quartz glass, as well as combinations or composite materials thereof. The preferred material of the solid support and/or its surface is polystyrene. The solid support may be in the form of a plate (e.g., an ELISA or ELISPOT plate, or a microtiter plate), a membrane (e.g., a blotting membrane), a slide, a bead or particle (e.g., a magnetic bead).

In the course of this assay, the novel blocking reagent is preferably used in a concentration range of about 0.01-5% (w/v), more preferably, about 0.25-4% (w/v), about 0.5-2% (w/v) or about 1% (w/v). It may be dissolved in water or a buffer, in particular, a physiological buffer system. In the context of the present invention, physiological buffers have a pH-value between 4 and 9 and include but are not limited to phosphate buffered saline, ammonium carbonate buffer, sulfonic acid based buffers, e.g., 4-2-hydroxyethyl-1-piperazineethanesulfonic acid (HEPES) buffer or piperazine-N,N'-bis(2-ethanesulfonic acid) (PIPES) buffer, amine based buffers, e.g., tris(hydroxymethyl) methylamine buffer (Tris) and glycine buffers.

The solution used as a novel blocking reagent may, in addition to the compound disclosed herein, also contain other blocking reagents, e.g., those known in the state of the art.

The present invention also provides a method for carrying out a qualitative and/or quantitative determination of an analyte in a sample with the method being based on specific binding between the analyte and a ligand thereof in a test system, wherein a) the analyte or the ligand is bound to a solid support, b) the solid support is brought into contact with the novel blocking reagent comprising a compound of Formula I as described in this specification, c) the solid support is brought into contact with either analyte or ligand, whichever has not been used in step a), d) binding between ligand and analyte is determined.

Optionally, washing steps may be carried out between different steps of the procedure. The compound of Formula I as described in the specification may additionally or alternatively be used as a component of the washing buffer and/or of the buffer containing the analyte or ligand in step c) of the procedure. A suitable concentration is about 0.01-5% (w/v), preferably, 0.25-4% (w/v) or, more preferably, 0.5-2% (w/v), e.g., in water or a buffer as described above.

Blocking of the solid support is preferably carried out for at least 15 min and up to several hours, e.g., about 30 min to 7 h or 8 h or overnight, or for about 1 h to 2 h. Blocking may be carried out, e.g., at 0-50° C., 4-37° C., 4-25° C. or 8-20° C., which may also depend on the stability of other reagents used. Methods of carrying out such an assay are well known in the state of the art.

Preferably, one or more of the specific compounds of Formula I, Formula II or Formula III disclosed herein is used. Preferred compounds that may be used as novel blocking reagents in the context of the invention are e.g., OA200 (N,N-di(α-methoxy[poly(ethyleneoxy)]ethyl)octadec-9-ene-1-amine (average molecular weight ~1.15 kDa)/Polyoxyethylen-20-oleylamine, Wall Chemie GmbH, Kempen, Del.) or DKA300 (N-(α-methoxy[poly(ethylene glycol)]ethyl)-dicocoamine (average molecular weight ~1.70 kDa)/Polyoxyethylen-30-dicocoamine, Wall Chemie GmbH, Kempen, Del.), or the compounds described in the Examples. Commercially available compounds that may also be used in the invention, e.g., ethoxylated alkyl amines, e.g., ethoxylated coco amine (commercially available as Ethomeen C/25, Akzo Nobel, Chicago, Ill., US), ethoxylated tallow amine (commercially available as Berol 38, Akzo Nobel, Chicago, Ill., US), ethoxylated tallow diamine (commercially available as Ethoduomeen T/25, Akzo Nobel, Chicago, Ill., US), ethoxylated soyamine (commercially available as Tomamine E-S-15, Airproducts, Allentown, Pa., US) or coco poly(15) oxyethylene methyl ammonium chloride (commercially available as Tomamine Q-C-15, Airproducts, Allentown, Pa., US), have been used in the state of the art, e.g., as detergents (Holdar (1995). Aqueous cleaning composition for parts washers. U.S. Pat. No. 5,460,753), as emulsifiers (Varadaraj et al. (2003). Ethoxylated alkyl amine emulsion compositions for fuel cell reformer start-up. WO 2003064564) or as additives for plastics (Enge (2008)). Use of ethoxylated alkylamines for modification of the surface tension of plastics. WO 2008034716).

The present invention provides specific novel compounds of Formula I as described above, which are suitable for use as novel blocking reagents. In specific novel embodiments of the invention, the compound is a compound of Formula II or a compound of Formula III:

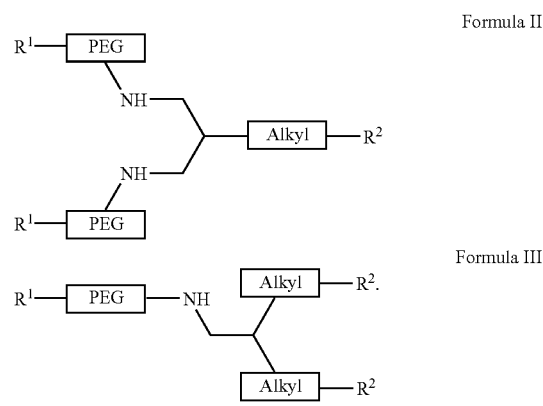

In these novel compounds, Alkyl may be a linear or branched, saturated or unsaturated alkylene group with an average chain length of 10-26 carbon atoms, preferably of 12-20 carbon atoms, and as described above. PEG may be a linear or branched poly(ethylene glycol) having an average molecular weight of 300-3,500 Da, preferably, 400-2,500 Da, and as described above. It is preferred that both Alkyl and PEG are linear. In case a compound comprises more than one Alkyl or PEG, molecular weights/length of units are specified for each unit separately.

$R^1$ is selected from the group comprising —H, —CH$_3$, —CH$_2$CH$_3$, —CH$_2$CH$_2$CH$_3$ and —CH(CH$_3$)$_2$, and $R^2$ is —H.

In one embodiment, the compound is a compound of Formula II and $R^1$ is —CH$_3$, $R_2$ is —H, PEG is linear poly (ethylene glycol) with an average molecular weight of 400-700 Da and Alkyl is —(CH$_2$)$_{12}$— or —(CH$_2$)$_{20}$—, i.e., compound 8a or 8a' as described in the Examples.

In another embodiment, the compound is a compound of Formula III and $R^1$ is —CH$_3$, $R^2$ is —H, PEG is linear poly (ethylene glycol) with an average molecular weight of 400-700 Da and Alkyl is —(CH$_2$)$_{12}$—, i.e., compound 8e as described in the Examples.

In another embodiment, the compound is a compound of Formula III and $R^1$ is —CH$_3$, $R^2$ is —H, PEG is linear poly (ethylene glycol) with an average molecular weight of 1,500-2,500 Da and Alkyl is —(CH$_2$)$_{20}$—, i.e., compound 8'e' as described in the Examples.

The novel blocking reagent may also comprise a salt, in particular an ammonium salt of any of the compounds of the invention, e.g., a halide, an acetate, a phosphate, a borate, a sulphate, a carbonate or a sulfonate.

The present invention also provides a kit comprising (a) a novel blocking reagent, which is a compound of Formula I as defined in the specification or a salt thereof, in particular one of the specifically defined compounds, and (b) a ligand intended for specific binding to the analyte. As described above, the ligand and/or analyte can, e.g., be a reagent selected from the group consisting of cells, oligo- or polynucleotides, nucleic acids, or, small molecules, lipids, oligo- or polysaccharides, oligo- or polypeptides, proteins, or derivatives or combinations of any of the aforementioned substances, wherein peptides and/or proteins may be glycosylated. Preferably the ligand and analyte is an oligo- or polypeptide or protein, e.g., an antibody or an antigen/hapten or a lectin, a carbohydrate-containing structure, e.g., a glycoprotein, or a receptor and/or a ligand thereof. In one embodiment, the kit comprises a novel blocking reagent of the invention and an antibody or a lectin. The kit may further comprise prefabricated buffers or concentrates facilitating their preparation and/or standards for analysis of samples and/or a description for carrying out the assay.

Use of the novel blocking reagents according to the invention in a solid phase assay system was surprisingly shown to be advantageous in saturating the solid phase surface and to prevent the unwanted adsorption of biological materials to the surface in subsequent incubations, which resulted in lower background signals in the assay due to reduction of NSB.

At the same time it was shown that the novel blocking reagents, surprisingly, are excellent at preserving the desired specific recognition process between ligand and analyte (e.g., antigen and antibody), leading to an improved sensitivity of the assay in comparison to state of the art blocking reagents.

The novel blocking reagents according to the invention are therefore able to improve the signal-to-noise (S/N) ratio of immunoassays by increasing both sensitivity and specificity in a broad range of setups.

Moreover, the novel blocking reagents according to the invention are more advantageous than state of the art blocking reagents of biological origin in that they are more stable, both as pure substance and in solution, and can thus be stored for long terms. They can be manufactured consistently from lot to lot. No cross-reactivity with any commonly applied detection system has been found. There is no reason for any import/export restrictions for these reagents.

Furthermore, the novel blocking reagents allow diagnostic applications based on glycan recognition. Currently no versatile and sophisticated commercial solid phase-supported test system is available for carbohydrates. This lack is mainly due to cross-reactivity of the state-of-the-art blocking reagents from biological sources, which almost always contain carbohydrate residues due to protein glycosylation and thus create false positive signals. The closing of this analytical gap by the novel blocking reagents according to the invention might be of particular interest for diagnostic purposes, e.g., to determine changes in the glycosylation pattern of analyte proteins which may occur during inflammation or infection. An analysis of these and other conditions could be possible with use of the novel blocking reagents, which contain no carbohydrate units.

As the assays in which the novel blocking reagents are used may be diagnostic assays, the present invention also relates to the compounds of Formula I described above as diagnostic reagents.

The advantageous effects of the novel blocking reagents according to the invention were demonstrated experimentally. The following examples describe the invention in more detail and support the above mentioned advantages of the novel blocking reagents of the invention. The examples are intended to illustrate, not to limit the invention. All literature cited herein is herewith expressly and completely incorporated.

EXAMPLES

Materials and buffers used in the examples were as following:

96 well half area polystyrene high binding microtiter plates, (Corning BV, Schiphol, Nebr.)

Nitrocellulose transfer membrane (0.2 µm, Schleicher & Schuell BioScience GmbH (Whatman Group), Dassel, Del.)

PVDF transfer membrane (0.2 µm, Whatman Inc., Sanford, Me., US)

D-PBS: Dulbecco's phosphate buffered saline (1.47 mM $KH_2PO_4$, 8.10 mM $Na_2HPO_4$, 137 mM NaCl, 2.68 mM KCl, pH 7.4)

L-PBS: Lite PBS (10.0 mM $NaH_2PO_4$ and 10.0 mM NaCl, titrated with NaOH to pH 7.0)

PBST: D-PBS containing 0.05% (v/v) Tween20 (Sigma-Aldrich Chemie, Munich, Del.)

TMB substrate solutions:
Solution A (205 mM citric acid, titrated with KOH to pH 4.0, 3.075 mM $H_2O_2$)
Solution B (41 mM 3,3'-tetramethylbenzidine and 8.1 mM tetrabutyl ammonium borohydride, dissolved in anhydrous, neat dimethylacetamide)

The following section contains a list of blocking solutions (BS1-8) prepared with state of the art blocking reagents:

BS1: BSA (bovine albumine fraction V; MP Biomedicals, Solon, Ohio, US), 1% (w/v) in D-PBS BS2: Fish gelatine (HighPure liquid gelatine; Norland Products, Cranbury, N.J., US), 1% (w/v) in D-PBS BS3: Tween20 (Sigma-Aldrich Chemie, Munich, Del.), 0.5% (v/v) in D-PBS BS4: Casein (Hammarsten grade, VWR International, Darmstadt, Del.), 1% (w/v) in D-PBS BS5: Casein hydrolysate, 1% (w/v) in D-PBS, prepared by the following procedure: 1 g casein (Hammarsten grade, VWR International, Darmstadt, Del.) was dissolved in 80 mL of 0.3 M aqueous NaOH at 37° C. and allowed to hydrolyse for several hours. Then 10 mL of a 10 fold concentrated D-PBS solution were added, the pH was set to 8 by addition of diluted HCl and the volume was adjusted with double distilled water to 100 mL.

BS6: Skimmed milk (Lactoland, Dülmen, Del.), 5% (w/v) in D-PBS

BS7: AquaBlock (commercially available fish plasma containing blocking reagent; EastCoastBio, North Berwick, Me., US), ready to use solution BS8: Rotiblock (commercially available PVP containing blocking reagent; Carl Roth, Karlsruhe, Del.), 10 fold diluted in double distilled water.

The next section contains a list of blocking solutions (BS9-30) prepared with novel blocking reagents according to the invention:

BS9: N-(α-methoxy[poly(ethylene oxy)]ethyl)-14-amino tetradecanamide (average molecular weight ~770 Da) 7f, 1% (w/v) in D-PBS BS10: N-(α-methoxy[poly(ethylene oxy)]ethyl)-22-amino docosanamide (average molecular weight ~890 Da) 7f', 1% (w/v) in D-PBS BS11: N-(α-methoxy[poly(ethylene oxy)]ethyl)-14-amino tetradecanamide (average molecular weight ~2.22 kDa) 7'f, 1% (w/v) in D-PBS BS12: N-(α-methoxy[poly(ethylene oxy)]ethyl)-22-amino docosanamide (average molecular weight ~2.34 kDa) 7'f', 1% (w/v) in D-PBS BS13: 14-(α-methoxy[poly(ethylene oxy)]ethoxy)tetradecane-1-amine (average molecular weight ~760 Da) 7g', 1% (w/v) in D-PBS BS14: 22-(α-methoxy[poly(ethylene oxy)]ethoxy) docosane-1-amine (average molecular weight ~870 Da) 7g', 1% (w/v) in D-PBS BS15: 14-(α-methoxy[poly(ethylene oxy)]ethoxy)tetradecane-1-amine (average molecular weight ~2.21 kDa) 7'g, 1% (w/v) in D-PBS BS16: N,N'-di(α-methoxy[poly(ethylene oxy)]ethyl)-2-dodecyl propane-1,3-diamine (average molecular weight ~1.31 kDa) 8a, 1% (w/v) in D-PBS BS17: N,N'-di(α-methoxy[poly(ethylene oxy)]ethyl)-2-eicosyl propane-1,3-diamine (average molecular weight ~1.42 kDa) 8a', 1% (w/v) in D-PBS BS18: N,N'-di(α-methoxy[poly(ethylene oxy)]ethyl)-2,2'-dieicosyl propane-1,3-diamine (average molecular weight ~1.70 kDa) 8b', 0.5% (w/v) in D-PBS BS19: N-(α-methoxy[poly(ethylene oxy)]ethyl)tetradecane-1-amine (average molecular weight ~750 Da) 8d, 1% (w/v) in D-PBS BS20: N-(α-methoxy[poly(ethylene oxy)]ethyl) docosane-1-amine (average molecular weight ~860 Da) 8d', 1% (w/v) in D-PBS BS21: N-(α-methoxy[poly(ethylene oxy)]ethyl)tetradecan-1-amine (average molecular weight ~2.20 kDa) 8'd, 1% (w/v) in D-PBS BS22: N-(α-methoxy[poly(ethylene oxy)]ethyl)docosan-1-amine (average molecular weight ~2.31 kDa) 8'd', 1% (w/v) in D-PBS BS23: N-(α-methoxy[poly(ethylene oxy)]ethyl)-2-dodecyl tetradecane-1-amine (average molecular weight ~910 Da) 8e, 1% (w/v) in D-PBS BS24: N-(α-methoxy[poly(ethylene oxy)]ethyl)-2-eicosyl docosane-1-amine (average molecular weight ~1.14 kDa) 8e', 0.2% (w/v) in D-PBS BS25: N-(α-methoxy[poly(ethylene oxy)]ethyl)-2-eicosyl docosane-1-amine (average molecular weight ~2.59 kDa) 8'e', 1% (w/v) in D-PBS BS26: N-(α-methoxy[poly(ethylene oxy)]ethyl)-14-amino tetradecane-1-amine (average molecular weight ~760 Da) 8f, 1% (w/v) in D-PBS BS27: N-(α-methoxy[poly(ethylene oxy)]ethyl)-22-amino docosane-1-amine (average molecular weight ~870 Da) 8f', 1% (w/v) in D-PBS BS28: N-(α-methoxy[poly(ethylene oxy)]ethyl)-14-amino tetradecane-1-amine (average molecular weight ~2.21 kDa) 8'f, 1% (w/v) in D-PBS BS29: OA200, 0.5% (w/v) in D-PBS; OA200: N,N-di(α-methoxy[poly(ethylene oxy)]ethyl)octadec-9-ene-1-amine (average molecular weight ~1.15 kDa)/Polyoxyethylen-20-oleylamine BS30: DKA300, 1% (w/v) in D-PBS; DKA300: N-(α-methoxy[poly(ethylene oxy)]ethyl)dicocoamine (average molecular weight ~1.70 kDa)/Polyoxyethylen-30-dicocoamine Conditions and abbreviations used:
room temperature: 25° C. (±5° C.)
o/n: over night (approx. 17 h)
ddH$_2$O: double distilled water Example 1

Specificity-ELISA

This ELISA was designed to detect the degree of NSB of antibodies from human serum to polystyrene plates which had been pretreated with different blocking solutions. As such, high signals indicate high NSB, resulting from poor blocking ability of the blocking reagent and low signals indicate low NSB, as a result of efficient blocking.

Human serum was prepared from a freshly collected blood sample from a healthy adult blood donor (the sampling of blood for this purpose was approved by the Ethics Committee of the Medical University of Lübeck). 250 mL blood was drawn and incubated o/n at room temperature. The clotted blood was then incubated on ice for 1 h and centrifuged for 10 min at an rcf of 1,800×g. The supernatant was divided sterilely in 1.5 mL portions. The aliquots were snap-frozen in liquid nitrogen and stored at −80° C.

High-binding polystyrene microtiter plates were blocked with 150 µL/well of a specific blocking solution (BS1-30) for 7 h at room temperature. After washing the plates four times with 150 µL/well D-PBS, 45 µL/well of a human serum solution (either 20% (v/v) or 2% (v/v) in the corresponding blocking solution) or the blocking solution alone as a negative control were added to each well and the plates were incubated o/n at 4° C. The plates were washed four times with 150 µL/well of D-PBS and incubated for 3 h at room temperature with 45 µl/well of 0.25 µg/mL of biotin-labelled goat anti-human IgG (Southern Biotech, Birmingham, Ala., US) in the corresponding blocking solution). The plates were washed six times with 150 µL/well of PBST and 45 µL/well of 1 µg/mL of horseradish-peroxidase-labelled streptavidin (Vector Laboratories, Burlingame, Calif., US) in the corresponding blocking solution were added. The plates were incubated for 90 min at room temperature. After washing the plates six times with 150 µL/well of PBST, 45 µL/well of a freshly prepared TMB substrate solution (5 mL solution A+125 µL solution B) were added and allowed to develop colour in the dark for 10 min at room temperature. The reaction was stopped by adding 75 µL of 1 M sulphuric acid to each well. Optical densities at 450 nm and 405 nm were measured with a microplate reader (Molecular Devices, Sunnyvale, Calif., USA).

The procedure was carried out independently in duplicate for BS9-28 and four times for BS1-8 and BS29-30. Results are summarised in FIG. 1. Due to a hook effect, signals at 20% (v/v) human serum are mostly lower than respective signals at 2% (v/v) human serum. All of the investigated novel blocking reagents perform as efficient as commercially available reagents. Many reagents (BS9, 13, 16, 20, 22 and 26) are as efficient as Aquablock or Rotiblock, which perform best of all commercially available reagents, but BS17 (8a') shows even better results and, thus, outcompetes all state of the art blocking reagents tested.

Example 2

Diagnostic ELISA 1—Prion Assay

This ELISA was designed to investigate the effect of different blocking reagents on the detection of prion protein (PrP) in reference samples. Low signals indicate a decreased sensitivity and vice versa.

For each blocking reagent six wells of high-binding polystyrene microtiter plates were coated o/n at 4° C. with 45 µL/well of a solution of a recombinant, His6-tagged prion protein fragment consisting of amino acids 90-231 of murine prion protein (PrP90-231) (Bade et al. (2006). Intranasal immunization of Balb/c mice against prion protein attenuates orally acquired transmissible spongiform encephalopathy. Vaccine 24:1242-1253), in a concentration of either 50 ng/mL or 3 ng/mL in L-PBS, or with L-PBS alone as a negative control o/n at 4° C. After washing the plates three times with 150 µL/well of PBST, the plates were blocked with 150

μL/well of a specific blocking solution (BS1-30) for 7 h at room temperature. The plates were washed four times with 150 μL/well of PBST and incubated o/n at 4° C. with 45 μL/well of 0.25 ng/mL monoclonal anti-PrP antibody clone 6H4 (Prionics, Schlieren, CH), in the corresponding blocking solution containing additional 0.1% (v/v) Tween20. The plates were washed four times with 150 μL/well of PBST and 45 μL/well of 1:2000 diluted horseradish-peroxidase-labelled goat anti-mouse IgG antibody (Southern Biotech, Birmingham, Ala., US) in the corresponding blocking solution were added. The plates were incubated for 90 min at room temperature. After washing the plates six times with 150 μL/well of PBST, 45 μL/well of a freshly prepared TMB substrate solution (5 mL solution A+125 μL solution B) were added to each well and allowed to develop colour in the dark for 10 min at room temperature. The reaction was stopped by adding 75 μL/well of 1 M sulphuric acid. Optical densities at 450 nm and 405 nm were measured with a microplate reader (Molecular Devices, Sunnyvale, Calif., USA).

Figure 2:
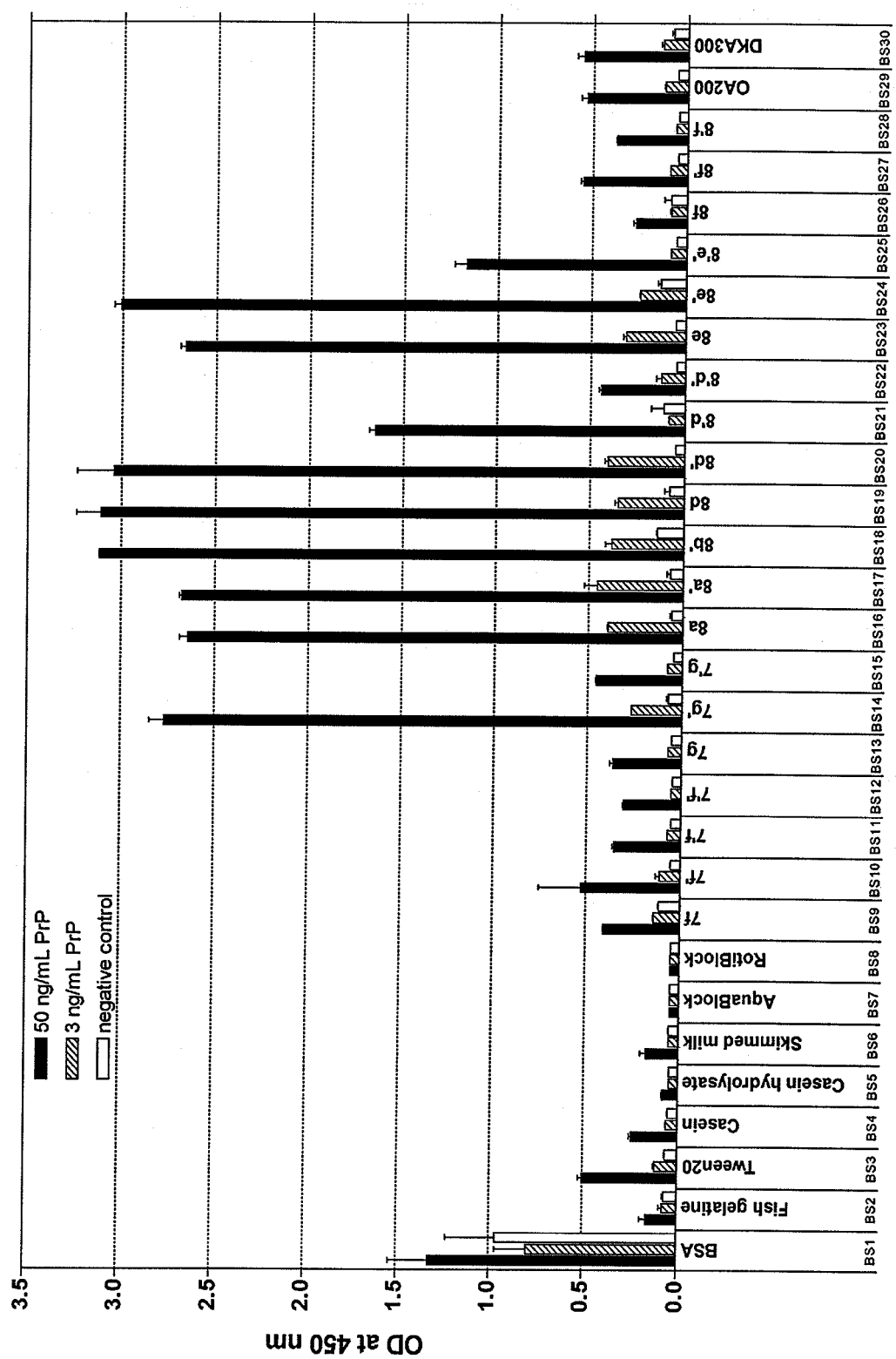
FIG. 2 shows the results of a Prion ELISA. Optical density at 50 and 3 ng/ml PrP in a Prion-ELISA is given. Bars indicate mean+/−standard error (N=2 for BS9-28, and N=4 for BS1-8 and BS29-30).

The procedure was carried out independently in duplicate for BS9-28 and four times for BS1-8 and BS29-30. Results are shown in FIG. 2. It is remarkable that some commercially available blocking reagents such as Aquablock or Rotiblock, which showed good results in NSB reduction (see example 1) perform poorly regarding the sensitivity. It appears that these reagents prevent any positive signals, no matter whether correct or false. A very high signal in the negative control indicates that BSA again was not able to sufficiently reduce NSB. In contrast to the commercially available reagents, all novel blocking reagents tested show distinct signals above background level at least at a PrP90-231 concentration of 50 ng/mL, many of them even at 3 ng/mL. Hence, most blocking reagents according to the invention are superior to state of the art blocking reagents in our experimental set-up.

Example 3

Diagnostic ELISA 2—Hepatitis B Assay

In some cases it is important that a test yields a high sensitivity not only at certain concentrations of the biomolecules to be detected, but at a whole range of concentrations. Here, we determined the signal strength of a positive control of Hepatitis B surface antigen (HBsAg) in a serial dilution with a typical direct sandwich assay.

High-binding polystyrene microtiter plates were coated with 45 μL/well of 0.5 μg/mL goat anti-HBsAg (AbD Serotec, Kidlington, Oxford, UK) in D-PBS o/n at 4° C. After washing the plates four times with 150 μL/well of D-PBS, plates were blocked for 3 h at room temperature with 150 μL/well of a specific blocking solution (BS1-30). The plates were washed four times with 150 μL/well of D-PBS and incubated for 2 h at room temperature with 45 μL/well (serial dilution, 20,000, 8,000, 3,200, 1,280, 512, 205, 82, 33, 13, 5 ng/mL) of recombinant HBsAg (AbD Serotec, Kidlington, Oxford, UK) in the corresponding blocking solution. The plates were washed four times with 150 μL/well of D-PBS followed by addition of 45 μL/well of 4 μg/mL of horseradish-peroxidase-labelled goat anti-HBsAg antibody (AbD Serotec, Kidlington, Oxford, UK) in the corresponding blocking solution). The plates were incubated for 60 min at room temperature. After washing the plates six times with 150 μL/well of PBST, 45 μL/well of a freshly prepared TMB substrate solution (5 mL solution A+125 μL solution B) were added and allowed to develop colour in the dark for 30 min at room temperature. The reaction was stopped by adding 75 μL/well of 1 M sulphuric acid. Optical densities at 450 nm and 405 nm were measured with a microplate reader (Molecular Devices, Sunnyvale, Calif., USA).

Figure 3:
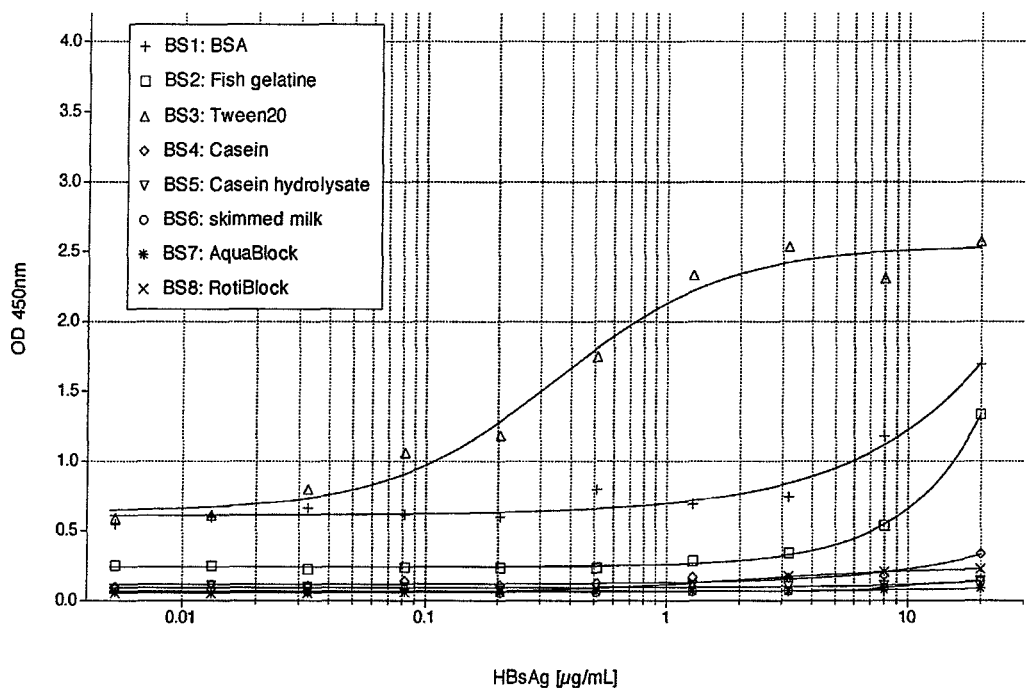
FIG. 3 shows the results of a Hepatitis B ELISA. Optical density against logarithmic HBsAg concentration is given. Values for each fitted curve refer to a single measurement of a serial dilution.
Figure 3:
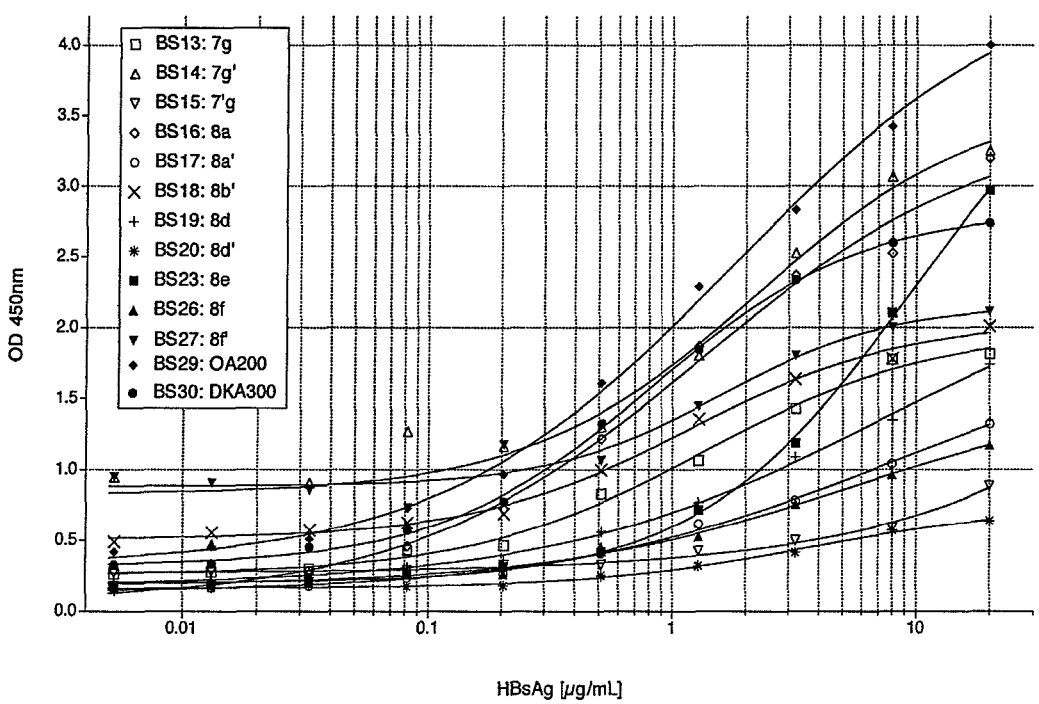

The assay was carried out once for BS9-28 and in duplicate for BS1-8 and BS29-30. Four parameter logistic functions were fitted to the raw data and optical density (OD) was plotted against the (logarithmic) HBsAg concentration (FIG. 3). The fit functions were analysed to yield quantitative data. The limit of detection was determined by t-statistics (95% confidence level) using the lower plateau of the logistic fit functions as background level (Frey et al. (1998). A statistically defined endpoint titer determination method for immunoassays. J. Immunol. Methods 221:35-41; Prism v 4.03, GraphPad Software, La Jolla, Calif., US). The inflexion point and the signal to noise ratio (defined here as the ratio of the maximum OD to the minimum OD of the four parameter curve) were also calculated (Table 1).

With almost all commercially available blocking solutions no signals above background could be achieved. With the commercial blocking solutions BS1 (BSA) and BS2 (Gelatine) the assay at least showed a potential onset of a sigmoidal curve at high concentrations of HBsAg. Only for the commercial blocking solution BS3 (Tween20) the assay yielded a complete sigmoidal curve with lower and upper plateau. In contrast to the majority of the commercial blocking reagents, the application of the blocking reagents according to the invention generated in more than half of the blocking solutions used increased signals, i.e., almost complete sigmoidal curves were achieved. The limit of detection was similar or lower (BS 13, 16, 17, 18, 19, 26, 29, or 30) compared to the commercial reagent Tween20, but the signal-to-noise ratio was equal (BS 14, 18, or 20) or 2-12fold higher (BS 13, 16, 17, 18, 19, 26, 29, or 30) with blocking reagents according to the invention. Hence, most blocking reagents according to the invention were superior to state of the art blocking reagents tested in our experimental set-up.

TABLE 1

Quantitative analysis of the Hepatitis B ELISA fitted curves

| Blocking reagent | | Limit of detection [μg/mL HBsAg] | Inflexion point [μg/mL HBsAg] | Signal to noise ratio at maximum OD |
|---|---|---|---|---|
| BS1 | BSA | n.d. [2] | n.d. [2] | n.d. [2] |
| BS2 | Gelatine | 0.569 | n.d. [3] | n.d. [3] |
| BS3 | Tween20 | 0.041 | 0.210 | 4.329 |
| BS4 | Casein | n.d. [1] | n.d. [1] | n.d. [1] |
| BS5 | Casein hydrolysate | n.d. [1] | n.d. [1] | n.d. [1] |
| BS6 | Skimmed milk | n.d. [1] | n.d. [1] | n.d. [1] |
| BS7 | AquaBlock | n.d. [1] | n.d. [1] | n.d. [1] |
| BS8 | RotiBlock | n.d. [1] | n.d. [1] | n.d. [1] |
| BS9 | 7f | n.d. [2] | n.d. [2] | n.d. [2] |
| BS10 | 7f' | n.d. [2] | n.d. [2] | n.d. [2] |
| BS11 | 7'f | n.d. [2] | n.d. [2] | n.d. [2] |
| BS12 | 7'f' | n.d. [1] | n.d. [1] | n.d. [1] |
| BS13 | 7g | 0.063 | 1.332 | 7.796 |
| BS14 | 7g' | 0.282 | 2.191 | 4.394 |
| BS15 | 7'g | 0.271 | n.d. [3] | n.d. [3] |
| BS16 | 8a | 0.052 | 1.299 | 53.094 |
| BS17 | 8a' | 0.032 | 8.408 | 15.603 |
| BS18 | 8b' | 0.061 | 1.159 | 4.043 |
| BS19 | 8d | 0.032 | 7.378 | 14.119 |
| BS20 | 8d' | 0.162 | 3.612 | 4.525 |
| BS21 | 8'd | n.d. [1] | n.d. [1] | n.d. [1] |
| BS22 | 8'd' | n.d. [1] | n.d. [1] | n.d. [1] |
| BS23 | 8e | 0.092 | 9.878 | 22.119 |
| BS24 | 8e' | n.d. [1] | n.d. [1] | n.d. [1] |
| BS25 | 8'e' | n.d. [1] | n.d. [1] | n.d. [1] |
| BS26 | 8f | 0.070 | 5.433 | 8.615 |
| BS27 | 8f' | 0.329 | 1.568 | 2.450 |

TABLE 1-continued

Quantitative analysis of the Hepatitis B ELISA fitted curves

| | Blocking reagent | Limit of detection [µg/mL HBsAg] | Inflexion point [µg/mL HBsAg] | Signal to noise ratio at maximum OD |
|---|---|---|---|---|
| BS28 | 8'f | n.d.[1] | n.d.[1] | n.d.[1] |
| BS29 | OA200 | 0.035 | 1.270 | 11.738 |
| BS30 | DKA300 | 0.018 | 0.771 | 9.164 | n.d.: [1] No significant sigmoidal curve distinguishable; [2] Background problems (negative control generated signals), fit curve accuracy too low ($R^2 < 0.95$); [3] inflexion point > 20 µg/mL HBsAg Example 4

Immunoblot

Immunoblots are another typical application for blocking reagents. In most cases, nitrocellulose and PVDF membranes are used in this type of experiments. In our experimental set-up, nitrocellulose membranes were used without any pre-treatment, the PVDF membranes were incubated with 750 µL of ethanol (1.63 mL/cm$^2$) for 1 min at room temperature before blocking.

Membranes (11.5 mm×4 mm) were blocked in 500 µL (1.1 mL/cm$^2$) of a specific blocking solution (BS1-30) or of D-PBS as negative control for 60 min at room temperature. The membranes were subsequently incubated for 60 min at room temperature with 500 µL (1.1 mL/cm$^2$) of 0.8 µg/mL AlexaFluor680-labelled goat anti-mouse IgG antibody (Invitrogen, Carlsbad, Calif., US) in the corresponding blocking solution or in D-PBS in case of the negative control. After incubation the membranes were washed six times with 750 µL (1.6 mL/cm$^2$) of D-PBS for 10 min at room temperature. Fluorescence was quantitated on a fluorescence imager with appropriate software (Odyssey Infrared Imager and Odyssey software V2.1, LI-COR Biosciences, Lincoln, Nebr., USA).

Figure 4:
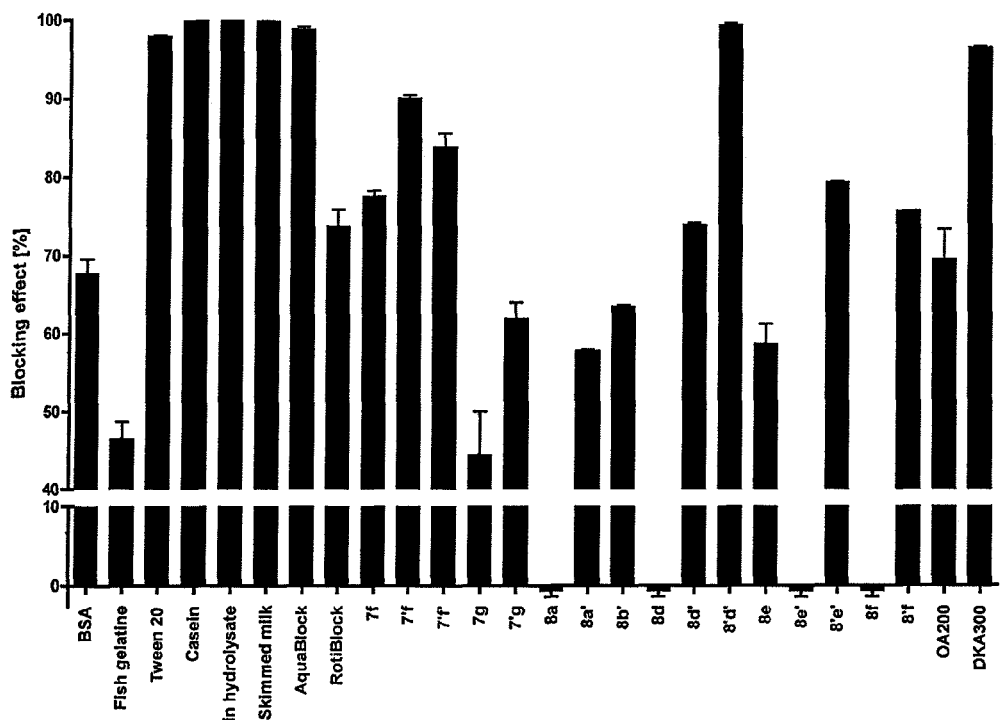
FIG. 4 shows the results of an Immunoblot. The fluorescence indicative for non-specific antibody binding was normalised linearly by defining the fluorescence of the negative control (no blocking reagent used) as 0% blocking effect and the lowest measured fluorescence as 100% blocking effect. Bars indicate mean+/−standard error (N=2 for all blocking solutions).
Figure 4:
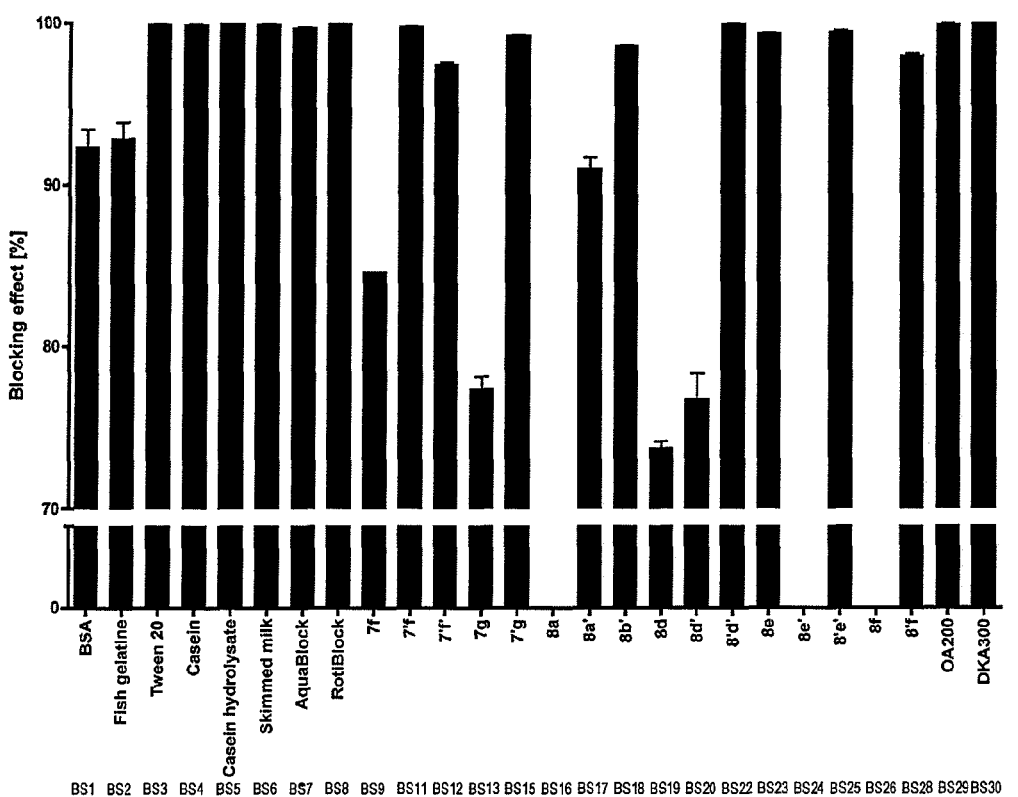

The procedure was carried out in duplicate for each membrane and blocking solution. The fluorescence measured was normalised linearly by defining the fluorescence of the negative control as 0% blocking effect and the lowest measured fluorescence as 100% blocking effect. Results are summarised in FIG. 4. For nitrocellulose membranes most of the blocking reagents according to the invention show a performance comparable to state of the art blocking reagents.

Example 5

Determination of Critical Micellar Concentrations (CMC)

The surface tension of 3 mL of a specific blocking solution (BS3 and BS9-30) was determined four times each for different concentrations. The highest concentration was 0.0033 g/mL and second highest 0.0025 g/mL blocking reagent in D-PBS. The latter solution (0.0025 g/mL) was 2 fold serially diluted (e.g., concentrations measured were 0.0033 g/mL, 0.0025 g/mL, 0.00125 g/mL, 0.000625 g/mL, 0.0003125 g/mL and so on), resulting in 8-13 different concentrations. The (uncorrected) surface tension was measured with a manual tensiometer (educational tensiometer K6, Krüss GmbH, Hamburg, Del.) and plotted against the logarithmic concentration. CMC was determined (via linear regression) as the intersection of the two linear parts on the surface tension versus log-transformed concentration curve. In some cases, no change was seen in the rate of surface tension decrease although the solutions were highly diluted and the surface tension already approached the value for D-PBS. In these cases we assume the CMC to be higher than 0.0033 g/mL.

TABLE 2

Critical micellar concentrations (CMC) for commercial blocking reagents (Tween20) and blocking reagents according to the invention

| | | CMC[1] [g/mL] | CMC [mM] |
|---|---|---|---|
| BS3 | Tween20 | 0.0000767 | 0.0625 |
| BS9 | 7f | 0.0013077 | 1.6983 |
| BS10 | 7f' | 0.0000716 | 0.0804 |
| BS11 | 7'f | >0.0033000[2] | n.d.[2] |
| BS12 | 7'f' | 0.0001010 | 0.0432 |
| BS13 | 7g | 0.0002903 | 0.3976 |
| BS14 | 7g' | n.d.[3] | n.d.[3] |
| BS15 | 7'g | >0.0033000[2] | n.d.[2] |
| BS16 | 8a | 0.0003447 | 0.2632 |
| BS17 | 8a' | 0.0001808 | 0.1273 |
| BS18 | 8b' | 0.0001091 | 0.0642 |
| BS19 | 8d | 0.0003812 | 0.5083 |
| BS20 | 8d' | 0.0000698 | 0.0831 |
| BS21 | 8'd | 0.0014124 | 0.6420 |
| BS22 | 8'd' | 0.0000994 | 0.0430 |
| BS23 | 8e | 0.0000971 | 0.1067 |
| BS24 | 8e' | 0.0000421 | 0.0369 |
| BS25 | 8'e' | 0.0007274 | 0.2809 |
| BS26 | 8f | 0.0022099 | 2.9077 |
| BS27 | 8f' | 0.0001020 | 0.1159 |
| BS28 | 8'f | >0.0033000[2] | n.d.[2] |
| BS29 | OA200 | 0.0000275 | 0.0239 |
| BS30 | DKA300 | 0.0001115 | 0.0664 |

Figure 5:
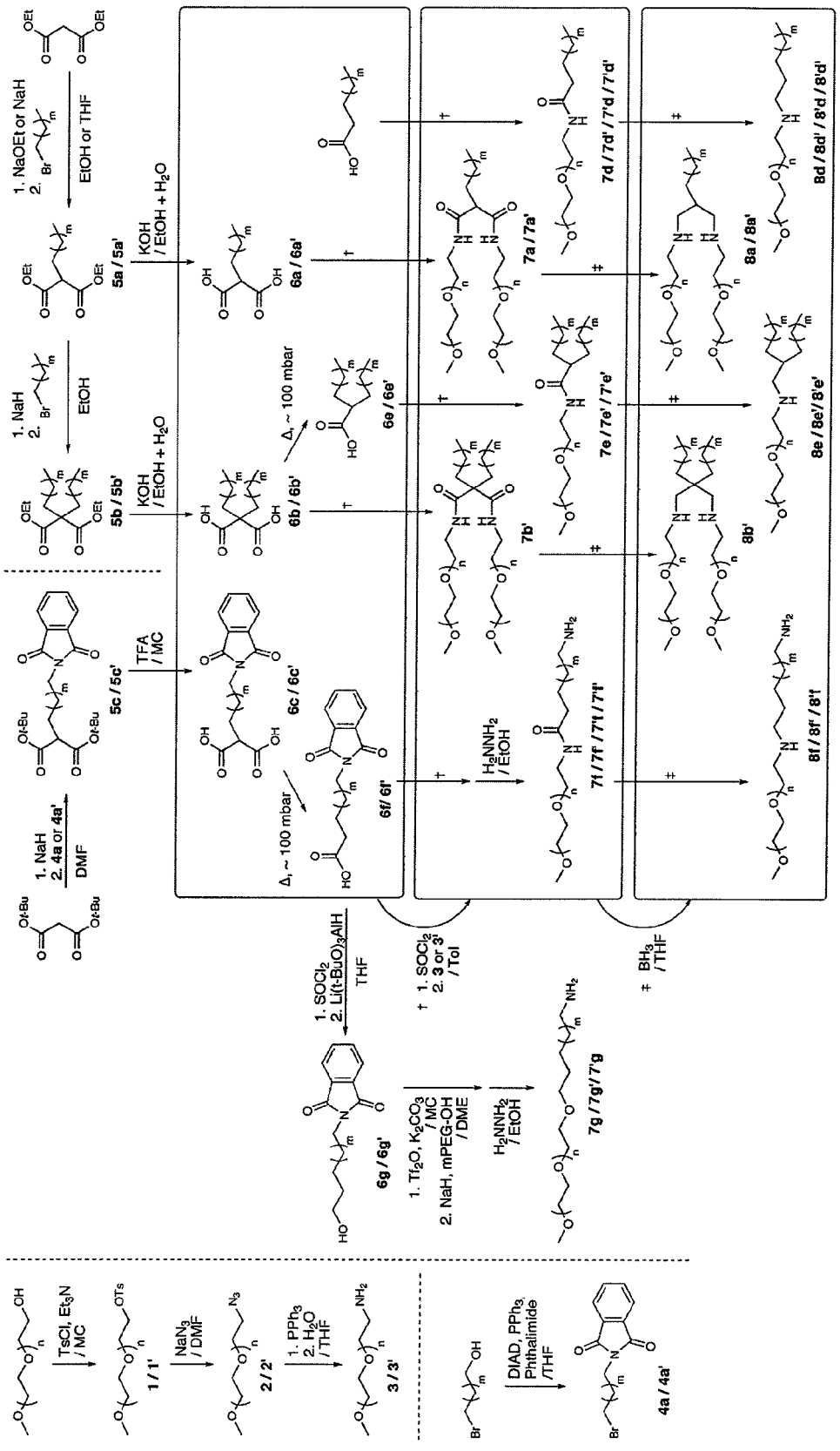
FIG. 5 shows the synthesis steps for the preparation of blocking reagents according to the invention. Structure abbreviations indicate the following: $n_{average}$=approx. 11 for no apostrophe after a number, $n_{average}$=approx. 44 for an apostrophe following a number; m=10 for no apostrophe after a letter, m=18 for an apostrophe following a letter.

[1]CMC data are uncorrected, i.e., correction factors for the surface tension due to temperature, geometry and/or density influences have not been used for calculation.
n.d.:[2] CMC not determined in the concentration range observed, supposedly higher than highest measured concentration (0.0033 g/mL); [3]not determined Chemical Syntheses General Remarks:

In FIG. 5 an overview of the syntheses employed for the preparation of the blocking reagents according to the invention is presented. The detailed description is given in general procedures A-K and examples 6-59. IUPAC recommendations for nomenclature were followed as closely as possible. It should be noted that, sometimes differing from the recommendations, some well-established trivial names were retained and ethylene oxide —$CH_2CH_2O$— was always chosen as the preferred constitutional repeating unit (CRU) to keep naming consistent, e.g., α-methoxy[poly(ethylene oxy)]ethyl- is a substituent constituting $CH_3O$—$(CH_2CH_2O)_n CH_2CH_2$—.

Column chromatography was performed on silica gel 60 (Carl Roth, Karlsruhe, Del.) if not stated otherwise. MALDI-TOF spectrometry was used to characterise derivatives containing polydisperse polymer units. As the molecular mass of the repetitive unit of poly(ethylene glycol) is approx. 44 Da, signals separated by a multiple of 44 Da refer to the same distribution. For each distinguishable distribution in one spectrum the central signal of the top three most abundant signals is given and the range of the (approx. bell-shaped) distribution is indicated (considering signals with at least an 0.1 fold count of the maximum signal) in parenthesis.

$^1$H and $^{13}$C NMR usually were measured in chloroform-d$_1$. Spectra of all amine containing compounds were described by the chemical shifts of the respective dominant form (either amine- or protonated (ammonium) form) as the shifts differ substantially. Cases where the shifts of the protonated form are reported are indicated.

General Procedure A

The respective alcohol and a 1.1-fold molar amount each of triphenylphosphine and phthalimide each were dissolved in anhydrous tetrahydrofuran. A 1.1-fold molar amount of diisopropyl azo dicarboxylate was added slowly while stirring and keeping the temperature at room temperature. The cooling was removed and the reaction mixture stirred for 2.5 h-1 d at room temperature. The reaction process was monitored via thin layer chromatography. The solvent was removed and the crude product was purified by column chromatography.

General Procedure B

The respective malonic ester was deprotonated by either dissolving it in ethanol and dropping the solution to a carefully prepared sodium ethanolate solution containing an equimolar amount of sodium in ethanol (B1) or dissolving it in an appropriate solvent (tetrahydrofuran or dimethylformamide) and adding the solution to an equimolar amount of sodium hydride in the respective solvent (B2) and subsequently stirring at room temperature-reflux for 10 min-5 h until hydrogen formation ceased. Then an equimolar amount of alkylbromide was added and the reaction mixture was stirred at room temperature-reflux for 3 h-1 d. The reaction progress was monitored by thin layer chromatography. The solvent was removed in vacuo and the residue was taken up in diethyl ether or ethyl acetate. The organic fractions were washed once with ddH$_2$O, dried over MgSO$_4$ and concentrated. The crude product was purified by column chromatography.

General Procedure C

The respective malonic acid diethyl ester was stirred at reflux for 4.5-6 h with a freshly prepared solution of an approx. four-fold excess of potassium hydroxide dissolved in a 1:2 mixture of ddH$_2$O and ethanol. The solvent was evaporated and the residue was taken up in ddH$_2$O. Concentrated hydrochloric acid (32% (w/v)) was added until the pH reached approx. 1. The aqueous phase was extracted four times with diethyl ether. The organic fractions were combined, dried over MgSO$_4$ and concentrated.

General Procedure D

The respective malonic acid di-tert-butyl ester was dissolved in dichloromethane and an approx. ten fold molar excess of tri-fluoroacetic acid was added. The solution was stirred at room temperature for 3 d and the reaction progress was monitored by thin layer chromatography. The solvent and any remaining tri-fluoroacetic acid and ester were removed in vacuo.

General Procedure E

The respective malonic acid was stirred at 150-160° C. at atmospheric pressure for 70 min-5 h and for further 1-5 h at reduced pressure (approx. 100 mbar) until gas formation ceased.

General Procedure F

The respective carboxylic acid or malonic acid was stirred at reflux with an eight- to twenty-fold molar excess of thionylchloride for 1.5-7.5 h. The volatiles were removed in vacuo and the residue was co-distilled with toluene. The crude product was used for the next step without further purification.

General Procedure G

The respective carboxylic acid chlorides were dissolved in anhydrous tetrahydrofuran and cooled to 0° C. An approx. 2.4 fold molar amount of lithium tri(tert-butoxy) aluminum hydride was added under argon atmosphere and vigorous stirring and the reaction mixture was stirred at 0° C. for 1 h and for further 80 min-2 h at room temperature. The reaction mixture then was poured into an excess of 0.1 M hydrochloric acid and the aqueous phase was extracted four times with ethyl acetate. The organic fractions were combined, dried over MgSO$_4$ and concentrated. The residue was purified by column chromatography.

General Procedure H

The respective carboxylic acid chloride and an equimolar amount of 3/3' or the respective malonic acid chlorides and a 2.0-fold molar amount of 3/3' were dissolved in toluene and stirred at room temperature for 5-30 min. An equimolar amount of triethylamine was added and the reaction mixture was stirred at 75° C. bath temperature for o/n-4 d. The reaction mixture was cooled to room temperature and the precipitate was filtered off and washed with toluene. The filtrate and the washing solutions were combined and washed once with 0.2 M HCl and once with saturated sodium bicarbonate solution. The organic fractions were combined, dried over MgSO$_4$ and concentrated.

General Procedure I

The respective ω-phthalimido alkan-1-ol was dissolved in anhydrous dichloromethane and cooled to 0° C. A 1.2-fold molar amount of trifluoromethane sulfonic acid anhydride was added dropwise under an argon atmosphere and the reaction mixture was stirred at 0° C. for 35-90 min. A 1.1-fold molar amount of 2-(α-methoxy[poly(ethylene oxy)])ethanol was dissolved in anhydrous dimethoxy ethane and freshly dried molecular sieves 4 Å as well as a 1.05-fold molar amount of sodium hydride were added. The dimethoxy ethane solution was stirred at room temperature for 50-90 min. Meanwhile the dichloromethane solution was filtered and the precipitate was washed with ice cold dichloromethane. The filtrate and the washing solution were combined and washed once with ice cold saturated sodium bicarbonate solution. The organic fractions were combined, dried over MgSO$_4$ and the solvent was removed in vacuo at a temperature not exceeding 30° C. The residue was dissolved in anhydrous dimethoxy ethane and added to the 2-(α-methoxy[poly(ethylene oxy)])ethanol solution. The reaction mixture was stirred at room temperature o/n-5 d, then it was filtered and the filtrate was concentrated. The residue was purified by column chromatography.

General Procedure J

The respective phthalimide was dissolved in ethanol with an approx. eight-fold molar excess of hydrazine monohydrate. The solution was stirred at reflux o/n-1 d. The solvent was evaporated and the residue was dissolved in 0.1 M hydrochloric acid. The aqueous phase was washed twice with ethyl acetate and then treated with neat sodium hydroxide until the pH reached 14. The aqueous phase was then extracted four times with dichloromethane. The organic fractions were combined, dried over MgSO$_4$ and concentrated.

General Procedure K

The respective carboxylic acid amide or malonic acid amide was dissolved in anhydrous tetrahydrofuran and added slowly under argon atmosphere at 0° C. to an 2.4- to 5.1-fold molar amount of 1 M borane in tetrahydrofuran. The solution was allowed to warm to room temperature and then stirred at reflux o/n-4 d. The reaction was stopped by adding a 0.9-fold molar amount of 6 M hydrochloric acid. The solvent was removed and the residue was dissolved in 1 M hydrochloric acid. The pH was adjusted to 14 using neat sodium hydroxide. The aqueous phase was extracted four times with dichloromethane. The organic fractions were combined, dried over MgSO$_4$ and concentrated.

Example 6

Preparation of α-methoxy[poly(ethylene oxy)]para-toluene sulfonate (Average Molecular Weight ~0.70 kDa): 1

100 mmol (55.0 g) of 2-(α-methoxy[poly(ethylene oxy)]) ethanol (average molecular weight ~550 Da, Sigma-Aldrich Chemie, Munich, Del.) were dissolved in 400 mL of anhydrous dichloromethane. Freshly dried molecular sieves 4 Å and 250 mmol (35.0 mL) of triethylamine were added and the solution was cooled to 0° C. 250 mmol (47.7 g) of para-toluene sulfonylchloride were added under exclusion of humidity. The mixture was stirred at 0° C. for 60 min, warmed to room temperature and stirred for another 80 min. The solvent was removed and the residue was taken up in toluene. The mixture was filtered and the residue was washed with toluene. The filtrate and the washing solution were combined and concentrated. The residue was dissolved in toluene and purified twice by column chromatography (1. toluene→dichloromethane→dichloromethane/triethylamine 19:1; 2. toluene→acetonitril). Yield 63%.

$^1$H-NMR (360 MHz, CDCl$_3$): δ 2.44 (s, 3H), 3.37 (s, 3H), 3.62 (m, polymer backbone), 4.15 (dd, 2H), 7.33 (d, 2H), 7.79 (d, 2H).

$^{13}$C-NMR (90 MHz, CDCl$_3$): δ 21.8, 59.2, 68.8, 69.4, 70.0-71.0, 72.1, 128.1, 129.9, 133.2, 144.9.

MALDI-TOF: 671.3 (451.3-891.7) [M+H]$^+$, 693.4 (473.2-913.6) [M+Na]$^+$, 709.4 (489.2-929.6) [M+K]$^+$

Example 7

Preparation of α-methoxy[poly(ethylene oxy)]para-toluene sulfonate (Average Molecular Weight ~2.15 kDa): 1'

50.0 mmol (100 g) of 2-(α-methoxy[poly(ethylene oxy)])ethanol (average molecular weight ~2 kDa, Sigma-Aldrich Chemie, Munich, Del.) were dissolved in 300 mL of anhydrous dichloromethane. Freshly dried molecular sieves 4 Å and 125 mmol (17.4 mL) of triethylamine were added and the solution was cooled to 0° C. 125 mmol (23.8 g) of para-toluene sulfonylchloride were added under exclusion of humidity. The mixture was stirred at 0° C. for 40 min, warmed to room temperature and further stirred o/n. The solvent was removed and the residue was taken up in toluene. The precipitate was filtered off and washed with toluene. The filtrate and the washing solution were combined and concentrated. The residue was taken up in dichloromethane and filtered over a small amount of silica gel. The silica gel was washed with dichloromethane. The filtrate and the washing solution were again combined and concentrated. The residue was precipitated by addition of diethyl ether. The precipitate was filtered, washed with diethyl ether and dissolved in dichloromethane. The precipitation and washing steps were repeated, and the precipitate was dried in vacuo. Yield 84%.

$^1$H-NMR (360 MHz, CDCl$_3$): δ 2.44 (s, 3H), 3.37 (s, 3H), 3.63 (m, polymer backbone), 4.15 (dd, 2H), 7.33 (d, 2H), 7.79 (d, 2H).

$^{13}$C-NMR (90 MHz, CDCl$_3$): δ 21.8, 59.1, 68.8, 69.3, 70.0-71.5, 72.1, 128.1, 129.9, 133.2, 144.9.

Example 8

Preparation of 2-(α-methoxy[poly(ethylene oxy)])ethyl azide (Average Molecular Weight ~575 Da): 2

41.9 mmol (29.5 g) of 1 and 62.9 mmol (4.09 g) of sodium azide were suspended in 80 mL of anhydrous dimethylformamide and stirred at reflux for 3 h and at room temperature for 1 d. The reaction mixture was cooled and the solvent was removed in vacuo. The residue was co-distilled twice with toluene and then taken up in a 1:1 solution of toluene and diethyl ether. The precipitate was filtered off and rinsed with more toluene. The filtrate and the washing solutions were combined, concentrated and taken up in diethyl ether. The precipitate was filtered off and rinsed with more diethyl ether. The filtrate and the washing solutions were combined, concentrated and dried in vacuo. Yield 95%. The crude product was used in the following step without further purification.

Example 9

Preparation of 2-(α-methoxy[poly(ethylene oxy)])ethyl amine (Average Molecular Weight ~550 Da): 3

40.0 mmol (23.0 g) of 2 were dissolved in 100 mL of anhydrous tetrahydrofuran and cooled to 0° C. 83.0 mmol (22.0 g) of triphenylphosphine were added and the mixture was stirred at 0° C. for 45 min. The mixture was allowed to warm to room temperature and stirred o/n. The reaction progress was followed by thin layer chromatography. 126 mmol (2.27 mL) of ddH$_2$O were added and the reaction mixture was further stirred for 3 h. The reaction mixture was concentrated in vacuo and the residue was diluted with ddH2O. The aqueous phase was acidified to pH 1 using 2 M HCl and washed once with toluene. The aqueous phase was adjusted to pH 13 using neat sodium hydroxide and extracted three times with dichloromethane. The dichloromethane fractions were combined, dried over MgSO$_4$ and concentrated in vacuo. Yield 86%.

$^1$H-NMR (360 MHz, CDCl$_3$): δ 2.89 (m, 2H), 3.37 (s, 3H), 3.63 (m, polymer backbone).

$^{13}$C-NMR (90 MHz, CDCl$_3$): δ 41.8, 59.1, 70.0-71.5, 72.1, 72.7.

Example 10

Preparation of 2-(α-methoxy[poly(ethylene oxy)])ethyl azide (Average Molecular Weight ~2.03 kDa): 2'

20.0 mmol (43.1 g) of 1' and 30.0 mmol (1.95 g) of sodium azide were suspended in 80 mL of anhydrous dimethylformamide and stirred at reflux for 60 min. The reaction mixture was cooled to room temperature and stirred o/n. The solvent was removed in vacuo and the residue was taken up in toluene. Insoluble components were removed by centrifugation (15-30 min; 1,700 rcf) and the supernatant was carefully transferred into a flask. The centrifugation pellet was resuspended in toluene and the above mentioned steps were repeated 3 times. The combined supernatants were concentrated and dried in vacuo. Yield 100%. The crude product was used in the following step without further purification.

Example 11

Preparation of 2-(α-methoxy[poly(ethylene oxy)])ethyl amine (Average Molecular Weight ~2.00 kDa): 3'

20.0 mmol (40.1 g) of 2' were dissolved in 85 mL of anhydrous tetrahydrofuran and cooled to 0° C. 40.0 mmol (10.5 g) of triphenylphosphine were added and the mixture was stirred at 0° C. for 20 min. The mixture was allowed to warm to room temperature and stirred for 3 d. The reaction progress was monitored by thin layer chromatography. 60.0 mmol (1.08 mL) of ddH$_2$O were added and the reaction mixture was stirred o/n. ddH$_2$O was added and the aqueous phase was washed with toluene once and extracted with dichloromethane three times. The dichloromethane fractions were combined, dried over MgSO$_4$ and concentrated in vacuo. Yield 96%.

$^1$H-NMR (360 MHz, CDCl$_3$): δ 3.17 (m, 2H), 3.37 (s, 3H), 3.63 (m, polymer backbone), 3.92 (dd, 2H).

$^{13}$C-NMR (90 MHz, CDCl$_3$): δ 41.0, 59.2, 70.0-71.5, 72.1.

MALDI-TOF: 2189.6 (1792.6-2717.7) [M+H]$^+$, 2211.6 (1814.6-2739.7) [M+Na]$^+$

Example 12

Preparation of N-(12-Bromododecyl)phthalimide: 4

Following general procedure A, 70.0 mmol (18.6 g) of 12-Bromododecan-1-ol, 77.0 mmol (20.2 g) of triphenylphosphine, 77.0 mmol (11.3 g) of phthalimide and 77.0 mmol (16.1 mL) of diisopropyl azo dicarboxylate were reacted in 350 mL of tetrahydrofuran for 2.5 h and the mixture was processed accordingly. The crude product was purified by column chromatography (cyclohexane/ethyl acetate 9:1). Yield 93%.

$^1$H-NMR (360 MHz, CDCl$_3$): δ 1.26 (m, 14H), 1.41 (m, 2H), 1.67 (m, 2H), 1.85 (m, 2H), 3.40 (t, 2H), 3.67 (t, 2H), 7.70 (m, 2H), 7.84 (m, 2H).

$^{13}$C-NMR (90 MHz, CDCl$_3$): δ 27.0, 28.3, 28.9-29.6, 33.0, 34.2, 38.2, 123.3, 132.4, 134.0, 168.6.

Example 13

Preparation of N-(20-Bromoeicosyl)phthalimide: 4'

Following general procedure A, 69.4 mmol (26.2 g) of 20-Bromoeicosan-1-ol, 76.3 mmol (20.0 g) of triphenylphosphine, 76.3 mmol (11.2 g) of phthalimide and 76.3 mmol (15.5 mL) of diisopropyl azo dicarboxylate were reacted in 300 mL of tetrahydrofuran for 1 d and the mixture was processed accordingly. The crude product was purified by column chromatography (toluene). Yield 66%.

$^1$H-NMR (360 MHz, CDCl$_3$): δ 1.24 (m, 30H), 1.42 (m, 2H), 1.67 (m, 2H), 1.85 (m, 2H), 3.40 (t, 2H), 3.67 (t, 2H), 7.70 (m, 2H), 7.84 (m, 2H).

$^{13}$C-NMR (90 MHz, CDCl$_3$): δ 27.0, 28.3, 28.8, 28.9-29.8, 33.0, 34.2, 38.3, 123.3, 132.4, 133.9, 168.6.

Example 14

Preparation of 2-dodecyl propane dioic acid diethyl ester 5a and 2,2'-bisdodecyl propane dioic acid diethyl ester: 5b 40.0 mmol (1.60 g) of sodium hydride in mineral oil (60% w/w) were washed with anhydrous hexane and reacted with 40.0 mmol (6.07 mL) of malonic acid diethyl ester in 50 mL of anhydrous tetrahydrofuran for 10 min at room temperature according to general procedure B2. The mixture then was reacted with 40 mmol (9.6 mL) of dodecylbromide in 50 mL of anhydrous tetrahydrofuran for 7 h at reflux and o/n at room temperature according to general procedure B. The reaction mixture was separated into two equal portions.

One portion was worked up with ethyl acetate as described (general procedure B). Column chromatography (cyclohexane/ethyl acetate 19:1) gave 5a with 35% yield.

27.5 mmol (1.10 g) of sodium hydride in mineral oil (60% w/w) were washed with anhydrous hexane and reacted with the other portion for 10 min at room temperature according to general procedure B2 (in deviation from this procedure, the mixture was used as provided without further dilution). The mixture then was reacted with 19 mmol (4.5 mL) of dodecylbromide for 6 h at reflux and o/n at room temperature. The work-up was performed as described (general procedure B) with ethyl acetate. Column chromatography (cyclohexane→cyclohexane/ethyl acetate 19:1) gave 5b with 35% yield.

5a: $^1$H-NMR (360 MHz, CDCl$_3$): δ 0.88 (t, 3H), 1.25 (m, 26H), 1.88 (dt, 2H), 3.30 (t, 1H), 4.19 (q, 4H).

$^{13}$C-NMR (90 MHz, CDCl$_3$): δ 14.2, 22.8, 27.5, 28.9-29.8, 32.0, 52.3, 61.4, 169.8.

5b: $^1$H-NMR (360 MHz, CDCl$_3$): δ 0.88 (t, 6H), 1.25 (m, 46H), 1.85 (m, 4H), 4.17 (q, 4H).

$^{13}$C-NMR (90 MHz, CDCl$_3$): δ 14.3, 22.8, 24.1, 29.5-29.9, 32.1, 32.3, 57.7, 61.0, 172.2.

Example 15

Preparation of 2-eicosyl propane dioic acid diethyl ester 5a' and 2,2'-biseicosyl propane dioic acid diethyl ester: 5b'

70.0 mmol (10.6 mL) of malonic acid diethyl ester in 10 mL of ethanol and 70.9 mmol (1.63 g) of sodium in 60 mL of ethanol were reacted for 30 min at reflux according to general procedure B1. The mixture then was reacted with 70.3 mmol (25.4 g) of eicosylbromide for 3 h at reflux according to general procedure B. The reaction mixture was separated into two equal portions.

One portion was worked up as described (general procedure B) with diethyl ether. Column chromatography (cyclohexane→cyclohexane/ethyl acetate 19:1) gave 5a' with 28% yield.

35.2 mmol (810 mg) of sodium were added to the other portion and the reaction mixture was stirred at reflux for 20 min. 35.0 mmol (12.7 g) of eicosylbromide were added and the reaction mixture was stirred at reflux o/n. The work-up was performed as described (general procedure B) with diethyl ether. Column chromatography (cyclohexane/ethyl acetate 19:1) gave 5b' with 37% yield.

5a': $^1$H-NMR (360 MHz, CDCl$_3$): δ 0.88 (t, 3H), 1.25 (m, 42H), 1.88 (dt, 2H), 3.31 (t, 1H), 4.19 (q, 4H).

$^{13}$C-NMR (90 MHz, CDCl$_3$): δ 14.3, 22.9, 27.5, 28.9-29.8, 32.1, 52.3, 61.4, 169.8.

5b': $^1$H-NMR (360 MHz, CDCl$_3$): δ 0.88 (t, 6H), 1.25 (m, 78H), 1.85 (m, 4H), 4.17 (q, 4H).

$^{13}$C-NMR (90 MHz, CDCl$_3$): δ 14.3, 22.8, 24.1, 29.5-29.9, 32.1, 32.3, 57.7, 61.0, 172.2.

Example 16

Preparation of 2-(12-phthalimido dodecyl)propane dioic acid di-tert-butyl ester: 5c 43.8 mmol (10.0 mL) of malonic acid di-tert-butyl ester and 43.8 mmol (1.91 g) of sodium hydride in mineral oil (55% (w/w)) were reacted in 70 mL of anhydrous dimethylformamide for 5 h at room temperature according to general procedure B2. 43.8 mmol (17.3 g) of 4 were added to the mixture and the reaction was stirred at room temperature o/n according to procedure B. The reaction mixture was separated into two equal portions.

One portion was worked up as described (general procedure B) with diethyl ether. Column chromatography (cyclohexane/acetone 19:1+0.1% (v/v) triethylamine) gave 5c with 36% yield.

¹H-NMR (360 MHz, CDCl₃): δ 1.24 (m, 18H), 1.45 (s, 18H), 1.65 (m, 2H), 1.78 (dt, 2H), 3.10 (t, 1H), 3.67 (t, 2H), 7.70 (m, 2H), 7.83 (m, 2H).
¹³C-NMR (90 MHz, CDCl₃): δ 27.0, 27.4, 28.1, 28.8-29.7, 38.2, 54.2, 81.2, 123.3, 132.4, 133.9, 168.6, 169.2.

Example 17

Preparation of 2-(20-phthalimido dodecyl)propane dioic acid di-tert-butyl ester: 5c'

29.3 mmol (6.56 mL) of malonic acid di-tert-butyl ester and 29.3 mmol (1.28 g) of sodium hydride in mineral oil (55% (w/w)) were reacted in 120 mL of anhydrous dimethylformamide for 50 min at room temperature according to general procedure B2. 45.4 mmol (23.0 g) of 4' were added to the mixture and the reaction mixture was stirred for 1 h at 75° C. bath temperature and at room temperature o/n. Additional 16.2 mmol (708 mg) of sodium hydride in mineral oil (55% (w/w)) were added and the reaction mixture was further stirred at room temperature for 7 h. The work-up was performed as described (general procedure B) with diethyl ether. Column chromatography (cyclohexane→cyclohexane/acetone 9:1) gave 5c' with 67% yield.
¹H-NMR (360 MHz, CDCl₃): δ 1.24 (m, 34H), 1.45 (s, 18H), 1.65 (m, 2H), 1.78 (dt, 2H), 3.10 (t, 1H), 3.67 (t, 2H), 7.70 (m, 2H), 7.84 (m, 2H).
¹³C-NMR (90 MHz, CDCl₃): δ 27.0, 27.4, 28.1, 28.8-29.9, 38.3, 54.2, 81.3, 123.3, 132.3, 134.0, 168.6, 169.2.

Example 18

Preparation of 2-dodecyl propane dioic acid: 6a

Following general procedure C, 87.8 mmol (4.93 g) of potassium hydroxide dissolved in 6 mL of ddH₂O and 12 mL of ethanol were reacted with 12.6 mmol (4.12 g) of 5a for 6 h and the mixture was processed accordingly. Yield 98%.
¹H-NMR (360 MHz, CDCl₃+DMSO-d₆): δ 0.83 (t, 3H), 1.20 (m, 20H), 1.86 (m, 2H), 3.25 (t, 1H).
¹³C-NMR (90 MHz, CDCl₃+DMSO-d₆): δ 14.1, 22.7, 27.4, 29.4-29.7, 31.9, 51.7, 172.3.

Example 19

Preparation of 2,2'-bisdodecyl propane dioic acid: 6b

Following general procedure C, 15 mmol (0.82 g) of potassium hydroxide dissolved in 1 mL of ddH₂O and 2 mL ethanol were reacted with 3.64 mmol (1.81 g) of 5b for 5.5 and the mixture was processed accordingly. Yield 97%.
¹H-NMR (360 MHz, CDCl₃): δ 0.88 (t, 6H), 1.25 (m, 40H), 1.93 (m, 4H).
¹³C-NMR (90 MHz, CDCl₃): δ 14.3, 22.8, 24.9, 29.4-29.8, 32.1, 35.6, 57.9, 177.3.

Example 20

Preparation of 2-eicosyl propane dioic acid: 6a'

Following general procedure C, 136 mmol (7.62 g) of potassium hydroxide dissolved in 10 mL of ddH₂O and 20 mL of ethanol were reacted with 19.4 mmol (8.56 g) of 5a' for 5.5 h and the mixture was processed accordingly. Yield 90%.
¹H-NMR (360 MHz, CDCl₃+DMSO-d₆): δ 0.76 (t, 3H), 1.14 (m, 36H), 1.76 (m, 2H), 3.15 (t, 1H).
¹³C-NMR (90 MHz, CDCl₃+DMSO-d₆): δ 14.0, 22.5, 27.3, 28.9-29.5, 31.7, 51.8, 171.9.

Example 21

Preparation of 2,2'-biseicosyl propane dioic acid: 6b'

Following general procedure C, 182 mmol (10.2 g) of potassium hydroxide dissolved in 13 mL of ddH₂O and 26 mL of ethanol were reacted with 26.0 mmol (18.7 g) of 5b' for 4.5 h and the mixture was processed accordingly. Yield 56%.
¹H-NMR (360 MHz, CDCl₃+DMSO-d₆): δ 0.79 (t, 6H), 1.17 (m, 72H), 1.80 (m, 4H).
¹³C-NMR (90 MHz, CDCl₃+DMSO-d₆): δ 14.1, 22.6, 24.9, 29.3-29.8, 31.9, 35.8, 57.3, 176.2.

Example 22

Preparation of 2-(12-phthalimido dodecyl)propane dioic acid: 6c

Following general procedure D, 16.0 mmol (8.45 g) of 5c and 160 mmol (11.9 mL) of trifluoroacetic acid were reacted in 12 mL of dichloromethane at room temperature and the mixture was processed. Yield 100%.
¹H-NMR (360 MHz, CDCl₃): δ 1.25 (m, 18H), 1.66 (m, 2H), 1.96 (dt, 2H), 3.45 (t, 1H), 3.68 (t, 2H), 7.70 (m, 2H), 7.85 (m, 2H).
¹³C-NMR (90 MHz, CDCl₃): δ 26.9, 27.2, 28.7-29.6, 38.3, 51.3, 123.4, 132.3, 134.1, 168.9, 174.1.

Example 23

Preparation of 2-(20-phthalimido eicosyl)propane dioic acid: 6c'

Following general procedure D, 19.5 mmol (12.5 g) of 5c' and 195 mmol (14.5 mL) of trifluoroacetic acid were reacted in 15 mL of dichloromethane at room temperature and the mixture was processed. Yield 100%.
¹H-NMR (360 MHz, CDCl₃): δ 1.25 (m, 18H), 1.67 (m, 2H), 1.96 (dt, 2H), 3.45 (t, 1H), 3.68 (t, 2H), 7.70 (m, 2H), 7.85 (m, 2H).
¹³C-NMR (90 MHz, CDCl₃): δ 27.0, 27.4, 28.8-29.8, 38.3, 51.2, 123.4, 132.3, 134.1, 168.8, 173.9.

Example 24

Preparation of 2-dodecyl tetradecanoic acid: 6e 7.01 mmol (3.09 g) of 6b were allowed to decarboxylate for 5 h at atmospheric pressure and 2.5 h at reduced pressure according to general procedure E. Yield 99%.
¹H-NMR (360 MHz, CDCl₃): δ 0.88 (t, 6H), 1.26 (m, 40H), 1.46 (m, 2H), 1.61 (m, 2H), 2.35 (m, 1H).
¹³C-NMR (90 MHz, CDCl₃): δ 14.3, 22.8, 27.5, 29.4-29.8, 32.1, 32.3, 45.5, 181.8.

Example 25

Preparation of 2-eicosyl docosanoic acid: 6e'

6.00 mmol (3.99 g) of 6b' were allowed to decarboxylate for 2 h at atmospheric pressure and 2 h at reduced pressure according to general procedure E. Yield 100%.
¹H-NMR (360 MHz, CDCl₃+DMSO-d₆): δ 0.70 (t, 6H), 1.08 (m, 40H), 1.24 (m, 2H), 1.40 (m, 2H), 2.08 (m, 1H).

$^{13}$C-NMR (90 MHz, CDCl$_3$+DMSO-d$_6$): δ 13.8, 22.3, 27.1, 29.0-29.3, 31.6, 32.1, 45.3, 178.3

Example 26

Preparation of 14-phthalimido tetradecanoic acid: 6f 10.0 mmol (4.18 g) of 6c were allowed to decarboxylate for 3 h at atmospheric pressure and 5 h at reduced pressure according to general procedure E. Yield 98%.

$^1$H-NMR (360 MHz, CDCl$_3$+DMSO-d$_6$): δ 1.05 (m, 18H), 1.40 (m, 2H), 1.47 (m, 2H), 2.06 (t, 2H), 3.47 (t, 2H), 7.53 (m, 2H), 7.64 (m, 2H).

$^{13}$C-NMR (90 MHz, CDCl$_3$+DMSO-d$_6$): δ 24.6, 26.5, 28.2-29.2, 33.9, 37.7, 122.8, 131.8, 133.6, 168.0, 175.6.

Example 27

Preparation of 22-phthalimido docosanoic acid: 6f'

9.00 mmol (4.77 g) of 6c' were allowed to decarboxylate for 70 min at atmospheric pressure and 1 h at reduced pressure and processed according to general procedure E. Yield 99%.

$^1$H-NMR (360 MHz, CDCl$_3$+DMSO-d$_6$): δ 1.24 (m, 32H), 1.67 (m, 4H), 2.35 (t, 2H), 3.67 (t, 2H), 7.70 (m, 2H), 7.84 (m, 2H).

$^{13}$C-NMR (90 MHz, CDCl$_3$+DMSO-d$_6$): δ 24.8, 27.0, 28.8-29.8, 34.0, 38.3, 123.3, 132.4, 134.0, 168.6, 178.9.

Example 28

Preparation of N-(14-hydroxy tetradecyl)phthalimide: 6g

Following general procedure F, 7.76 mmol (2.90 g) of 6f and 155 mmol (11.3 mL) of thionyl chloride were reacted for 5 h and the mixture was processed.

Following general procedure G, 5.76 mmol (2.26 g) of the crude acid chloride, 50 mL of anhydrous tetrahydrofuran and 13.6 mmol (3.46 g) of lithium tri(tert-butoxy) aluminum hydride were reacted at 0° C. and for 80 min at room temperature, and the mixture was processed accordingly. Column chromatography (cyclohexane/acetone 3:1) gave a yield of 76% over two steps.

$^1$H-NMR (360 MHz, CDCl$_3$): δ 1.25 (m, 16H), 1.56 (m, 2H), 1.67 (m, 2H), 3.64 (t, 2H), 3.67 (t, 2H), 7.70 (m, 2H), 7.84 (m, 2H).

$^{13}$C-NMR (90 MHz, CDCl$_3$): δ 25.9, 27.0, 28.8-29.7, 33.0, 38.3, 63.3, 123.3, 132.4, 134.0, 168.6.

Example 29

Preparation of N-(22-hydroxy docosyl)phthalimide: 6g'

Following general procedure F, 8.89 mmol (4.32 g) of 6f' and 180 mmol (13.2 mL) of thionyl chloride were reacted for 7 h and the mixture was processed.

Following general procedure G, 4.88 mmol (2.46 g) of the crude acid chloride, 50 mL of anhydrous tetrahydrofuran and 11.5 mmol (2.93 g) of lithium tri(tert-butoxy) aluminum hydride were reacted at 0° C. and for 2 h at room temperature and the mixture was processed accordingly. Column chromatography (dichloromethane/methanol 95:5) gave a yield of 70% over two steps.

$^1$H-NMR (360 MHz, CDCl$_3$): δ 1.25 (m, 32H), 1.56 (m, 2H), 1.67 (m, 2H), 3.64 (t, 2H), 3.67 (t, 2H), 7.70 (m, 2H), 7.84 (m, 2H).

Example 30

Preparation of N,N'-di(α-methoxy[poly(ethylene oxy)]ethyl)-2-dodecyl propane-1,3-diamide (Average Molecular Weight ~1.33 kDa): 7a Following general procedure F, 4.00 mmol (1.09 g) of 6a and 160 mmol (11.7 mL) of thionyl chloride were reacted for 5 h and the mixture was processed.

Following general procedure H, the crude malonic acid chloride was reacted with 8.01 mmol (4.39 g) of 3 in 20 mL of toluene for 30 min and with 7.9 mmol (1.1 mL) of triethylamine for 1 d and the mixture was processed accordingly. Yield 64%. The crude product was used in the following step without further purification.

Example 31

Preparation of N,N'-di(α-methoxy[poly(ethylene oxy)]ethyl)-2-eicosyl propane-1,3-diamide (Average Molecular Weight ~1.45 kDa): 7a'

Following general procedure F, 2.99 mmol (1.15 g) of 6a' and 120 mmol (8.75 mL) of thionyl chloride were reacted for 5 h and the mixture was processed.

Following general procedure H, the crude malonic acid chloride was reacted with 6.0 mmol (3.30 g) of 3 in 15 mL of toluene for 30 min and with 6.0 mmol (0.84 mL) of triethylamine o/n and the mixture was processed accordingly. Yield 74%. The crude product was used in the following step without further purification.

Example 32

Preparation of N,N'-di(α-methoxy[poly(ethylene oxy)]ethyl)-2,2'-dieicosyl propane-1,3-diamide (Average Molecular Weight ~1.73 kDa): 7b'

Following general procedure F, 2.03 mmol (1.33 g) of 6b' and 80 mmol (5.8 mL) of thionyl chloride were reacted for 5 h and the mixture was processed.

Following general procedure H, the crude malonic acid chloride was reacted with 4.01 mmol (2.20 g) of 3 in 20 mL of toluene for 5 min and with 4.0 mmol (0.56 mL) of triethylamine o/n and the mixture was processed accordingly. Yield 78%. The crude product was used in the following step without further purification.

Example 33

Preparation of N-(α-methoxy[poly(ethylene oxy)]ethyl)tetradecanamide (Average Molecular Weight ~760 Da): 7d Following general procedure F, 4.00 mmol (942 mg) of myristic acid (97% purity, TCI Europe, Zwijndrecht, BE) and 80 mmol (5.8 mL) of thionyl chloride were reacted for 3.5 h the mixture was and processed.

Following general procedure H, 2.0 mmol (0.49 g) of the crude acid chloride were reacted with 2.00 mmol (1.10 g) of 3 in 15 mL of toluene for 40 min and with 2.0 mmol (0.28 mL) of triethylamine for 2 d and the mixture was processed accordingly. Yield 89% over two steps. The crude product was used in the following step without further purification.

Example 34

Preparation of N-(α-methoxy[poly(ethylene oxy)]ethyl)docosanamide (Average Molecular Weight ~870 Da): 7d'

Following general procedure F, 3.01 mmol (1.08 g) of behenic acid (95% purity, TCI Europe, Zwijndrecht, BE) and 60 mmol (4.4 mL) of thionyl chloride were reacted for 5 h and the mixture was processed.

Following general procedure H, the crude acid chloride was reacted with 3.0 mmol (1.6 g) of 3 in 5 mL of toluene for 30 min and with 3.0 mmol (0.42 mL) of triethylamine for 4 d and the mixture was processed accordingly. Yield 80%. The crude product was used in the following step without further purification.

Example 35

Preparation of N-(α-methoxy[poly(ethylene oxy)]ethyl)tetradecanamide (Average Molecular Weight ~2.21 kDa): 7'd Following general procedure F, 4.00 mmol (942 mg) of myristic acid (97% purity, TCI Europe, Zwijndrecht, BE) and 80 mmol (5.8 mL) of thionyl chloride were reacted for 3.5 h and the mixture was processed. Following general procedure H, 2.0 mmol (0.49 g) of the crude acid chloride were reacted with 2.00 mmol (4.00 g) of 3' in 15 mL of toluene for 40 min and with 2.0 mmol (0.28 mL) of triethylamine for 2 d and the mixture was processed accordingly. Yield 87% over two steps. The crude product was used in the following step without further purification.

Example 36

Preparation of N-(α-methoxy[poly(ethylene oxy)]ethyl)docosanamide (Average Molecular Weight ~2.32 kDa): 7'd'

Following general procedure F, 4.01 mmol (1.44 g) of behenic acid (95% purity, TCI Europe, Zwijndrecht, BE) and 80 mmol (5.8 mL) of thionyl chloride were reacted for 1.5 h and the mixture was processed. Following general procedure H, 2.0 mmol (0.72 g) of the crude acid chloride were reacted with 2.00 mmol (4.00 g) of 3' in 10 mL of toluene for 40 min and with 2.0 mmol (0.28 mL) of triethylamine for 1 d and the mixture was processed accordingly. Yield 52% over two steps. The crude product was used in the following step without further purification.

Example 37

Preparation of N-(α-methoxy[poly(ethylene oxy)]ethyl)-2-dodecyl tetradecanamide (Average Molecular Weight ~930 Da): 7e Following general procedure F, 2.00 mmol (793 mg) of 6e and 40.4 mmol (2.95 mL) of thionyl chloride were reacted for 5 h and the mixture was processed.

Following general procedure H, the crude acid chloride was reacted with 2.00 mmol (1.10 g) of 3 in 7 mL of toluene for 20 min and with 2.0 mmol (0.28 mL) of triethylamine for 1 d and the mixture was processed accordingly. Yield 90%. The crude product was used in the following step without further purification.

Example 38

Preparation of N-(α-methoxy[poly(ethylene oxy)]ethyl)-2-eicosyl docosanamide (Average Molecular Weight ~1.15 kDa): 7e'

Following general procedure F, 2.01 mmol (1.25 g) of 6e' and 40.4 mmol (2.95 mL) of thionyl chloride were reacted for 5 h and the mixture was processed.

Following general procedure H, the crude acid chloride was reacted with 2.00 mmol (1.10 g) of 3 in 5 mL of toluene for 1 h and with 2.0 mmol (0.28 mL) of triethylamine for 1 d and the mixture was processed accordingly. Yield 89%. The crude product was used in the following step without further purification.

Example 39

Preparation of N-(α-methoxy[poly(ethylene oxy)]ethyl)-2-eicosyl docosanamide (Average Molecular Weight ~2.60 kDa): 7'e'

Following general procedure F, 2.00 mmol (1.25 g) of 6e' and 40.0 mmol (2.92 mL) of thionyl chloride were reacted for 6.5 h and the mixture was processed.

Following general procedure H, the crude acid chloride was reacted with 2.00 mmol (4.00 g) of 3' in 10 mL of toluene for 30 min and with 2.0 mmol (0.28 mL) of triethylamine for 2 d and the mixture was processed accordingly. Yield 76%. The crude product was used in the following step without further purification.

Example 40

Preparation of N-(α-methoxy[poly(ethylene oxy)]ethyl)-14-amino tetradecanamide (Average Molecular Weight ~770 Da): 7f Following general procedure F, 2.01 mmol (750 mg) of 6f and 40.4 mmol (2.95 mL) of thionyl chloride were reacted for 7.5 h the mixture was and processed.

Following general procedure H, the crude acid chloride was reacted with 2.00 mmol (1.10 g) of 3 in 10 mL of toluene for 20 min and with 2.0 mmol (0.28 mL) of triethylamine for 2 d and the mixture was processed accordingly. The resulting product was treated with 15 mmol (0.72 mL) of hydrazine monohydrate for 1 d, and the reaction mixture was processed, both according to general procedure J. Yield 72%.

1H-NMR (360 MHz, CDCl$_3$): δ 1.26 (m, 18H), 1.54 (m, 2H), 1.60 (m, 2H), 2.16 (t, 2H), 2.77 (t, 2H), 3.36 (s, 3H), 3.43 (m, 2H), 3.64 (m, polymer backbone).

13C-NMR (90 MHz, CDCl$_3$): δ 25.8, 26.9, 29.4-29.5, 36.8, 39.2, 41.3, 59.1, 70.1-70.6, 72.0, 173.5.

MALDI-TOF: 785.6 (564.8-961.7) [M+H]$^+$

Example 41

Preparation of N-(α-methoxy[poly(ethylene oxy)]ethyl)-22-amino docosanamide (Average Molecular Weight ~890 Da): 7f'

Following general procedure F, 8.89 mmol (4.32 g) of 6f' and 180 mmol (13.2 mL) of thionyl chloride were reacted for 7 h and the mixture was processed.

Following general procedure H, 2.00 mmol (1.01 g) of the crude acid chloride were reacted with 2.00 mmol (1.10 g) of 3 in 10 mL of toluene for 10 min and with 2.0 mmol (0.28 mL) of triethylamine for 4 d and the mixture was processed accordingly. The resulting product was treated with 15 mmol (0.71 mL) of hydrazine monohydrate for 1 d, and the reaction mixture was processed, both according to general procedure J. Yield 70% over two steps.

$^1$H-NMR (360 MHz, CDCl$_3$, protonated form): δ 1.24 (m, 34H), 1.61 (m, 2H), 1.68 (m, 2H), 2.17 (m, 2H), 2.89 (m, 2H), 3.37 (s, 3H), 3.44 (m, 2H), 3.65 (m, polymer backbone).

$^{13}$C-NMR (90 MHz, CDCl$_3$, protonated form): δ 25.9, 26.8, 27.1, 29.3-30.4, 36.8, 39.3, 40.3, 59.2, 70.1-70.7, 72.1, 173.6.

MALDI-TOF: 897.7 (677.7-1073.8) [M+H]$^+$

Example 42

Preparation of N-(α-methoxy[poly(ethylene oxy)]ethyl)-14-amino tetradecanamide (Average Molecular Weight ~2.22 kDa): 7'f Following general procedure F, 7.76 mmol (2.90 g) of 6f and 155 mmol (11.3 mL) of thionyl chloride were reacted for 5 h and the mixture was processed.

Following general procedure H, 2.00 mmol (785 mg) of the crude acid chloride were reacted with 2.00 mmol (4.00 g) of 3' in 10 mL of toluene for 40 min and with 2.0 mmol (0.28 mL) of triethylamine for 4 d and the mixture was processed accordingly. The resulting product was treated with 13 mmol (0.63 mL) of hydrazine monohydrate for 1 d, and the reaction mixture was processed, both according to general procedure J. Yield 64% over two steps.

$^1$H-NMR (360 MHz, CDCl$_3$): δ 1.24 (m, 18H), 1.48 (m, 2H), 1.60 (m, 2H), 2.16 (t, 2H), 2.72 (t, 2H), 3.36 (s, 3H), 3.43 (m, 2H), 3.63 (m, polymer backbone).

$^{13}$C-NMR (90 MHz, CDCl$_3$): δ 25.8, 27.0, 29.3-29.6, 36.8, 39.3, 41.8, 59.1, 69.7-70.7, 72.1, 173.3.

MALDI-TOF: 2371.4 (2063.2-2856.1) [M+H]$^+$

Example 43

Preparation of N-(α-methoxy[poly(ethylene oxy)]ethyl)-22-amino docosanamide (Average Molecular Weight ~2.34 kDa): 7'f'

Following general procedure F, 8.89 mmol (4.32 g) of 6f' and 180 mmol (13.2 mL) of thionyl chloride were reacted for 7 h and the mixture was processed.

Following general procedure H, 2.00 mmol (1.01 g) of the crude acid chloride were reacted with 2.00 mmol (4.00 g) of 3' in 10 mL of toluene for 10 min and with 2.0 mmol (0.28 mL) of triethylamine for 4 d and the mixture was processed accordingly. The resulting product was treated with 14 mmol (0.67 mL) of hydrazine monohydrate for 1 d, and the reaction mixture was processed, both according to general procedure J. Yield 58% over two steps.

$^1$H-NMR (360 MHz, CDCl$_3$, protonated form): δ 1.24 (m, 34H), 1.60 (m, 2H), 1.70 (m, 2H), 2.16 (m, 2H), 2.90 (m, 2H), 3.36 (s, 3H), 3.43 (m, 2H), 3.63 (m, polymer backbone).

$^{13}$C-NMR (90 MHz, CDCl$_3$, protonated form): δ 25.9, 26.6, 27.7, 29.1-29.8, 36.8, 39.3, 40.3, 59.1, 70.1-70.7, 72.1, 173.5.

MALDI-TOF: 2439.2 (2219.2-2880.4) [M+H]$^+$

Example 44

Preparation of 14-(α-methoxy[poly(ethylene oxy)]tetradecane-1-amine (Average Molecular Weight ~760 Da): 7g According to general procedure I, 2.00 mmol (663 mg) of 6g were reacted with 2.7 mmol (0.45 mL) of trifluoromethane sulfonic acid anhydride in 10 mL of dichloromethane for 35 min. At the same time 2.20 mmol (1.21 g) of 2-(α-methoxy[poly(ethylene oxy)])ethanol (average molecular weight ~550 Da, Sigma-Aldrich Chemie, Munich, Del.) were reacted with 2.42 mmol (335 mg) of anhydrous potassium carbonate and with 2.2 mmol (94 mg) of sodium hydride suspended in mineral oil (55% w/w) in 10 mL of anhydrous dimethoxyethane for 50 min. The dichloromethane solution was worked up, the resulting residue was dissolved in 10 mL of anhydrous dimethoxyethane, added to the 2-(α-methoxy[poly(ethylene oxy)])ethanolate solution, and the mixture was reacted o/n and processed, all according to general procedure I. The crude product was purified by column chromatography (dichloromethane/methanol 95:5). The resulting product was treated with 4.7 mmol (0.23 mL) of hydrazine monohydrate for 1 d, and the reaction mixture was processed, both according to general procedure J. Yield 23%.

$^1$H-NMR (360 MHz, CDCl$_3$): δ 1.25 (m, 16H), 1.56 (m, 4H), 2.79 (m, 2H), 3.37 (s, 3H), 3.44 (m, 2H), 3.64 (m, polymer backbone).

$^{13}$C-NMR (90 MHz, CDCl$_3$): δ 26.2, 26.9, 28.8-29.7, 30.9, 41.3, 59.2, 70.2, 70.4-70.8, 71.6, 72.1.

MALDI-TOF: 772.3 (596.3-948.4) [M+H]$^+$

Example 45

Preparation of 22-(α-methoxy[poly(ethylene oxy)]docosane-1-amine (Average Molecular Weight ~870 Da): 7g'

According to general procedure I, 3.00 mmol (1.42 mg) of 6g' were reacted with 3.6 mmol (0.60 mL) of trifluoromethane sulfonic acid anhydride in 25 mL of dichloromethane for 1.5 h. At the same time 2.10 mmol (1.16 g) of 2-(α-methoxy[poly(ethylene oxy)])ethanol (average molecular weight ~550 Da, Sigma-Aldrich Chemie, Munich, Del.) were reacted with 3.60 mmol (498 mg) of anhydrous potassium carbonate and with 1.4 mmol (60 mg) of sodium hydride suspended in mineral oil (55% (w/w)) in 15 mL of anhydrous dimethoxyethane for 1.5 h. The dichloromethane solution was worked up, the resulting residue was dissolved in 10 mL of anhydrous dimethoxyethane, added to the 2-(α-methoxy[poly(ethylene oxy)])ethanolate solution, and the mixture was reacted for 4 d and processed, all according to general procedure I. The crude product was purified by column chromatography (dichloromethane/methanol 9:1). The resulting product was treated with 9.9 mmol (0.49 mL) of hydrazine monohydrate o/n, and the reaction mixture was processed, both according to general procedure J. Yield 14%.

MALDI-TOF: 884.9 (620.8-1149.0) [M+H]$^+$, 906.9 (686.8-1171.0) [M+Na]$^+$

Example 46

Preparation of 14-(α-methoxy[poly(ethylene oxy)]tetradecane-1-amine (Average Molecular Weight ~2.21 kDa): 7'g According to general procedure I, 2.00 mmol (663 mg) of 6g were reacted with 2.5 mmol (0.42 mL) of trifluoromethane sulfonic acid anhydride in 10 mL of dichloromethane for 70 min. At the same time 2.20 mmol (4.40 g) of 2-(α-methoxy[poly(ethylene oxy)])ethanol (average molecular weight ~2.0 kDa, Sigma-Aldrich Chemie, Munich, Del.) were reacted with 2.45 mmol (338 mg) of anhydrous potassium carbonate and with 2.2 mmol (94 mg) of sodium hydride suspended in mineral oil (55% (w/w)) in 15 mL of dimethoxyethane for 50 min. The dichloromethane solution was worked up, the resulting residue was dissolved in 10 mL of anhydrous dimethoxyethane, added to the 2-(α-methoxy[poly(ethylene oxy)])ethanolate solution, and the mixture was reacted for 5 d and processed, all according to general procedure I. The crude product was purified by column chromatography (dichloromethane/methanol 9:1). The resulting product was treated with 16 mmol (0.79 mL) of hydrazine monohydrate o/n, and the reaction mixture was processed, both according to general procedure J. Yield 25%.

$^1$H-NMR (360 MHz, CDCl$_3$, protonated form): δ 1.26 (m, 16H), 1.56 (m, 2H), 1.67 (m, 2H), 2.91 (m, 2H), 3.45 (m, 2H), 3.63 (m, polymer backbone).

$^{13}$C-NMR (90 MHz, CDCl$_3$, protonated form): δ 26.1, 26.8, 27.7, 29.1-29.7, 40.3, 59.2, 70.2, 70.4-70.7, 71.6, 72.1.

MALDI-TOF: 2138.0 (1608.7-2666.4) [M+H]$^+$, 2160.0 (1762.7-2688.4) [M+Na]$^+$

Example 47

Preparation of N,N'-di(α-methoxy[poly(ethylene oxy)]ethyl)-2-dodecyl propane-1,3-diamine (Average Molecular Weight ~1.31 kDa): 8a 2.56 mmol (3.42 g) of 7a' dissolved in 25 mL of anhydrous tetrahydrofuran and 12.0 mmol (12.0 mL) of 1 M borane in tetrahydrofuran were reacted o/n and the mixture was processed, both according to general procedure K. The crude product was purified by column chromatography (Sephadex LH20, ethanol). Yield 45%.

$^1$H-NMR (360 MHz, CDCl$_3$, protonated form): δ 0.87 (t, 3H), 1.25 (m, 24H), 2.63 (m, 2H), 2.85 (m, 2H), 3.02 (m, 2H), 3.10 (m, 2H), 3.37 (s, 6H), 3.64 (m, polymer backbone).

$^{13}$C-NMR (90 MHz, CDCl$_3$, protonated form): δ 14.3, 22.8, 26.9, 29.5-29.9, 31.5, 32.1, 33.8, 48.1, 55.1, 59.2, 68.0, 70.4-70.7, 72.1.

MALDI-TOF: 1371.8 (1195.7-1591.9) [M+H]$^+$

Example 48

Preparation of N,N'-di(α-methoxy[poly(ethylene oxy)]ethyl)-2-eicosyl propane-1,3-diamine (Average Molecular Weight ~1.42 kDa): 8a'

2.20 mmol (3.19 g) of 7a' dissolved in 20 mL of anhydrous tetrahydrofuran and 10.3 mmol (10.3 mL) of 1 M borane in tetrahydrofuran were reacted o/n and the mixture was processed, both according to general procedure K. The crude product was purified by column chromatography (Sephadex LH20, ethanol). Yield 63%.

$^1$H-NMR (360 MHz, CDCl$_3$, protonated form): δ 0.88 (t, 3H), 1.25 (m, 24H), 2.64 (m, 2H), 2.86 (m, 2H), 3.02 (m, 2H), 3.12 (m, 2H), 3.37 (s, 6H), 3.63 (m, polymer backbone).

$^{13}$C-NMR (90 MHz, CDCl$_3$, protonated form): δ 14.3, 22.8, 26.9, 29.4-30.0, 31.5, 32.1, 33.8, 48.1, 55.1, 59.2, 68.0, 70.4-70.7, 72.1.

MALDI-TOF: 1351.8 (1087.8-1660.0) [M+H]$^+$

Example 49

Preparation of N,N'-di(α-methoxy[poly(ethylene oxy)]ethyl)-2,2'-dieicosyl propane-1,3-diamine (Average Molecular Weight ~1.70 kDa): 8b'

1.57 mmol (2.71 g) of 7b' dissolved in 20 mL of anhydrous tetrahydrofuran and 8.0 mmol (8.0 mL) of 1 M borane in tetrahydrofuran were reacted for 1 d and the mixture was processed, both according to general procedure K. Yield 99%.

$^1$H-NMR (360 MHz, CDCl$_3$+DMSO-d$_6$): δ 0.87 (t, 6H), 1.25 (m, 76H), 2.83 (m, 4H), 2.93 (m, 4H), 3.37 (s, 6H), 3.55 (m, 4H), 3.64 (m, polymer backbone), 3.95 (m, 4H).

$^{13}$C-NMR (90 MHz, CDCl$_3$+DMSO-d$_6$): δ 14.3, 22.7, 29.5-30.1, 32.1, 33.4, 37.8, 39.4, 48.3, 56.6, 59.2, 68.0, 70.4-70.7, 72.1.

Example 50

Preparation of N-(α-methoxy[poly(ethylene oxy)]ethyl)tetradecane-1-amine (Average Molecular Weight ~750 Da): 8d 1.79 mmol (1.36 g) of 7d dissolved in 15 mL of anhydrous tetrahydrofuran and 5.1 mmol (5.1 mL) of 1 M borane in tetrahydrofuran were reacted for 2 d and the mixture was processed, both according to general procedure K. The crude product was purified by column chromatography (dichloromethane→dichloromethane/methanol 9:1). Yield 32%.

$^1$H-NMR (360 MHz, CDCl$_3$): δ 0.88 (t, 3H), 1.25 (m, 18H), 1.67 (m, 2H), 2.83 (m, 2H), 3.02 (m, 2H), 3.37 (s, 3H), 3.64 (m, polymer backbone), 3.79 (m, 2H).

$^{13}$C-NMR (90 MHz, CDCl$_3$): δ 14.3, 22.8, 27.2, 29.4-29.8, 32.1, 48.3, 49.0, 59.2, 67.8, 70.3-70.7, 72.1.

MALDI-TOF: 756.8 (536.8-932.8) [M+H]$^+$, 778.8 (602.8-954.7) [M+Na]$^+$

Example 51

Preparation of N-(α-methoxy[poly(ethylene oxy)]ethyl)docosane-1-amine (Average Molecular Weight ~860 Da): 8d'

2.25 mmol (1.96 g) of 7d' dissolved in 25 mL of anhydrous tetrahydrofuran and 5.4 mmol (5.4 mL) of 1 M borane in tetrahydrofuran were reacted for 3 d and the mixture was processed, both according to general procedure K. The crude product was purified by column chromatography (dichloromethane→dichloromethane/methanol 9:1). Yield 24%.

$^1$H-NMR (360 MHz, CDCl$_3$, protonated form): δ 0.87 (t, 3H), 1.25 (m, 18H), 1.81 (m, 2H), 2.94 (m, 2H), 3.12 (m, 2H), 3.37 (s, 3H), 3.64 (m, polymer backbone), 3.89 (m, 2H).

$^{13}$C-NMR (90 MHz, CDCl$_3$, protonated form): δ 14.3, 22.8, 26.4, 27.0, 29.3-29.9, 32.1, 47.6, 48.5, 59.2, 66.5, 70.3-70.7, 72.1.

MALDI-TOF: 868.7 (648.6-1044.8) [M+H]$^+$

Example 52

Preparation of N-(α-methoxy[poly(ethylene oxy)]ethyl)tetradecane-1-amine (Average Molecular Weight ~2.20 kDa): 8'd 1.73 mmol (3.83 g) of 7'd dissolved in 20 mL of anhydrous tetrahydrofuran and 4.9 mmol (4.9 mL) of 1 M borane in tetrahydrofuran were reacted for 2 d and the mixture was processed, both according to general procedure K. The crude product was purified by column chromatography (dichloromethane→dichloromethane/methanol 9:1). Yield 4%.

$^1$H-NMR (360 MHz, CDCl$_3$, protonated form): δ 0.88 (t, 3H), 1.26 (m, 18H), 1.84 (m, 2H), 2.96 (m, 2H), 3.15 (m, 2H), 3.38 (s, 3H), 3.64 (m, polymer backbone), 3.93 (m, 2H).

$^{13}$C-NMR (90 MHz, CDCl$_3$, protonated form): δ 14.3, 22.8, 26.1, 26.9, 29.2-29.8, 32.1, 47.7, 48.3, 59.2, 65.9, 70.1-70.7, 72.1.

MALDI-TOF: 2342.7 (1990.2-2783.1) [M+H]$^+$, 2364.8 (2100.2-2761.1) [M+Na]$^+$

Example 53

Preparation of N-(α-methoxy[poly(ethylene oxy)]ethyl)docosane-1-amine (Average Molecular Weight ~2.31 kDa): 8'd'

1.00 mmol (2.32 g) of 7'd' dissolved in 20 mL of anhydrous tetrahydrofuran and 2.8 mmol (2.8 mL) of 1 M borane in tetrahydrofuran were reacted for 4 d and the mixture was processed, both according to general procedure K. The crude product was purified by column chromatography (dichloromethane→dichloromethane/methanol 9:1). Yield 22%.

$^1$H-NMR (360 MHz, CDCl$_3$, protonated form): δ 0.87 (t, 3H), 1.25 (m, 34H), 1.84 (m, 2H), 2.97 (m, 2H), 3.16 (m, 2H), 3.37 (s, 3H), 3.64 (m, polymer backbone), 3.92 (m, 2H).

$^{13}$C-NMR (90 MHz, CDCl$_3$, protonated form): δ 14.3, 22.8, 26.1, 26.9, 29.3-29.8, 32.1, 47.6, 48.3, 59.2, 65.9, 70.1-70.7, 72.1.

MALDI-TOF: 2278.2 (1750.1-2807.6) [M+H]$^+$, 2364.8 (2100.2-2761.1) [M+Na]$^+$

Example 54

Preparation of N-(α-methoxy[poly(ethylene oxy)]ethyl)-2-dodecyl tetradecane-1-amine (Average Molecular Weight ~910 Da): 8e 1.79 mmol (1.66 g) of 7e dissolved in 17 mL of anhydrous tetrahydrofuran and 5.0 mmol (5.0 mL) of 1 M borane in tetrahydrofuran were reacted for 1 d and the mixture was processed, both according to general procedure K. The crude product was purified by column chromatography (dichloromethane→dichloromethane/methanol 9:1). Yield 42%.

$^1$H-NMR (360 MHz, CDCl$_3$): δ 0.88 (t, 6H), 1.26 (m, 44H), 1.70 (m, 1H), 2.71 (m, 2H), 2.99 (m, 2H), 3.38 (s, 3H), 3.64 (m, polymer backbone).

$^{13}$C-NMR (90 MHz, CDCl$_3$): δ 14.3, 22.8, 26.5, 29.5-30.1, 31.8, 32.1, 36.6, 48.8, 52.8, 59.2, 70.4-70.8, 72.1.

MALDI-TOF: 924.9 (792.8-1056.9) [M+H]$^+$, 946.9 (858.9-1078.9) [M+Na]$^+$

Example 55

Preparation of N-(α-methoxy[poly(ethylene oxy)]ethyl)-2-eicosyl docosane-1-amine (Average Molecular Weight ~1.14 kDa): 8e'

1.79 mmol (2.06 g) of 7e' dissolved in 15 mL of anhydrous tetrahydrofuran and 5.0 mmol (5.0 mL) of 1 M borane in tetrahydrofuran were reacted o/n and the mixture was processed, both according to general procedure K. The crude product was purified by column chromatography (dichloromethane→dichloromethane/methanol 9:1). Yield 75%.

$^1$H-NMR (360 MHz, CDCl$_3$, protonated form): δ 0.88 (t, 6H), 1.25 (m, 76H), 1.92 (m, 1H), 2.90 (m, 2H), 3.19 (m, 2H), 3.38 (s, 3H), 3.64 (m, polymer backbone), 3.94 (m, 2H).

$^{13}$C-NMR (90 MHz, CDCl$_3$, protonated form): δ 14.3, 22.8, 26.2, 29.5-30.2, 31.3, 32.1, 35.1, 48.0, 51.8, 59.2, 65.6, 70.3-70.7, 72.1.

MALDI-TOF: 1148.6 (972.6-1324.6) [M+H]$^+$, 1214.6 (1038.6-1390.6) [M+Na]$^+$

Example 56

Preparation of N-(α-methoxy[poly(ethylene oxy)]ethyl)-2-eicosyl docosane-1-amine (Average Molecular Weight ~2.59 kDa): 8'e'

1.45 mmol (3.77 g) of 7'e' dissolved in 20 mL of anhydrous tetrahydrofuran and 5.5 mmol (5.5 mL) of 1 M borane in tetrahydrofuran were reacted for 3 d and the mixture was processed, both according to general procedure K. The crude product was purified by column chromatography (dichloromethane→dichloromethane/methanol 9:1). Yield 23%.

$^1$H-NMR (360 MHz, CDCl$_3$, protonated form): δ 0.88 (t, 6H), 1.25 (m, 76H), 1.92 (m, 1H), 2.90 (m, 2H), 3.19 (m, 2H), 3.38 (s, 3H), 3.64 (m, polymer backbone), 3.94 (m, 2H).

$^{13}$C-NMR (90 MHz, CDCl$_3$, protonated form): δ 14.3, 22.8, 26.2, 29.5-30.1, 31.3, 32.1, 35.1, 48.1, 51.8, 59.2, 65.6, 70.2-70.7, 72.1.

MALDI-TOF: 2690.6 (2426.5-3131.4) [M+H]$^+$, 2756.6 (2492.5-3197.9) [M+Na]$^+$

Example 57

Preparation of N-(α-methoxy[poly(ethylene oxy)]ethyl)-14-amino tetradecane-1-amine (Average Molecular Weight ~760 Da): 8f 1.30 mmol (1.00 g) of 7f dissolved in 13 mL of anhydrous tetrahydrofuran and 4.8 mmol (4.8 mL) of 1 M borane in tetrahydrofuran were reacted for 3 d and the mixture was processed, both according to general procedure K. The crude product was purified by column chromatography (dichloromethane/methanol 9:1→dichloromethane/methanol 9:1+0.1% (v/v) triethylamine). Yield 31%.

$^1$H-NMR (360 MHz, CDCl$_3$): δ 1.26 (m, 16H), 1.54 (m, 2H), 1.59 (m, 2H), 2.69 (t, 2H), 2.77 (t, 2H), 2.87 (t, 2H), 3.38 (s, 3H), 3.64 (m, polymer backbone).

$^{13}$C-NMR (90 MHz, CDCl$_3$): δ 26.9, 27.2, 28.8-29.7, 31.8, 41.6, 48.8, 49.7, 59.2, 69.3, 70.4-70.8, 72.1.

MALDI-TOF: 771.6 (551.5-996.7) [M+H]$^+$

Example 58

Preparation of N-(α-methoxy[poly(ethylene oxy)]ethyl)-22-amino docosane-1-amine (Average Molecular Weight ~870 Da): 8f'

1.25 mmol (1.11 g) of 7f' dissolved in 15 mL of anhydrous tetrahydrofuran and 3.75 mmol (3.75 mL) of 1 M borane in tetrahydrofuran were reacted for 4 d and the mixture was processed, both according to general procedure K. The crude product was purified by column chromatography (dichloromethane/methanol 9:1→dichloromethane/methanol 9:1+0.1% (v/v) triethylamine). Yield 17%.

$^1$H-NMR (360 MHz, CDCl$_3$, protonated form): δ 1.25 (m, 32H), 1.80 (m, 4H), 3.00 (m, 4H), 3.14 (m, 2H), 3.38 (s, 3H), 3.64 (m, polymer backbone).

$^{13}$C-NMR (90 MHz, CDCl$_3$, protonated form): δ 26.1, 26.9, 27.0, 27.7, 28.7-29.8, 40.5, 47.3, 48.9, 59.2, 66.3, 70.2-70.8, 72.1.

MALDI-TOF: 839.6 (663.5-1015.7) [M+H]$^+$

Example 59

Preparation of N-(α-methoxy[poly(ethylene oxy)]ethyl)-14-amino tetradecane-1-amine (Average Molecular Weight ~2.21 kDa): 8'f 1.20 mmol (2.67 g) of 7'f dissolved in 13 mL of anhydrous tetrahydrofuran and 4.5 mmol (4.5 mL) of 1 M borane in tetrahydrofuran were reacted for 3 d and the mixture was processed, both according to general procedure K. The crude product was purified by column chromatography (Sephadex LH20, ethanol). Yield 60%.

$^1$H-NMR (360 MHz, CDCl$_3$): δ 1.27 (m, 16H), 1.70 (m, 2H), 1.77 (m, 2H), 2.82 (m, 2H), 2.88 (m, 2H), 3.00 (m, 2H), 3.37 (s, 3H), 3.64 (m, polymer backbone).

$^{13}$C-NMR (90 MHz, CDCl$_3$): δ 26.5, 26.7, 28.3-29.6, 40.7, 48.1, 49.2, 59.2, 70.3-70.8, 72.1.

MALDI-TOF: 2400.4 (2136.5-2841.2) [M+H]$^+$

REFERENCES

Studentsov et al. (2002). J. Clin. Microbiol. 40:1755-1760
Harkins et al. (1930). J. Colloid Interface Sci. 52: 1751-1772
Holdar (1995). U.S. Pat. No. 5,460,753
Varadaraj et al. (2003). WO 2003064564
Enge (2008). WO 2008034716
Bade et al. (2006). Vaccine 24:1242-1253
Frey et al. (1998). J. Immunol. Methods 221:35-41

What is claimed is:

1. A blocking reagent comprising a compound of Formula II:

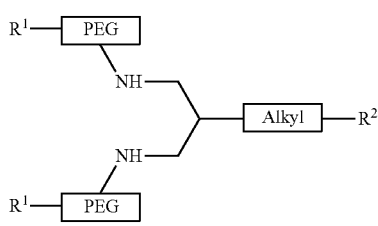

Formula II wherein R$^1$ is a residue selected from the group consisting of —H, —CH$_3$—CH$_2$CH$_3$, —CH$_2$CH$_2$CH$_3$ and —CH(CH$_3$)$_2$, PEG is a linear poly(ethylene glycol) having an average molecular weight of at least 300 Da, Alkyl is a linear alkylene moiety —(CH$_2$)$_n$— wherein n is 10-25, and R$^2$ is H, or a salt of a compound of Formula II.

2. The compound of Formula II of claim 1, wherein

PEG is a linear poly(ethylene glycol) having an average molecular weight of 300-3,500 Da, preferably, 400-2,500 Da, and R$^1$ is selected form the group consisting of —H, —CH$_3$, —CH$_2$CH$_3$, —CH$_2$CH$_2$CH$_3$ and —CH(CH$_3$)$_2$ and R$^2$ is —H.

3. The compound of Formula II of claim 1, wherein R$^1$ is —CH$_3$, R$^2$ is —H, PEG is a linear poly(ethylene glycol) with an average molecular weight of 400-700 Da and Alkyl is —(CH$_2$)$_{12}$— or —(CH$_2$)$_{20}$—.

* * * * *